(12) United States Patent
Assegehegn et al.

(10) Patent No.: US 11,975,102 B2
(45) Date of Patent: May 7, 2024

(54) ALL-IN-ONE LYOPHILIZED MULTIVITAMIN EMULSION FOR PARENTERAL APPLICATION

(71) Applicant: Fresenius Kabi Deutschland GmbH, Bad Homburg (DE)

(72) Inventors: Getachew Assegehegn, Friedberg (DE); Edmundo Brito De La Fuente, Bad Homburg (DE); Crispulo Gallegos-Montes, Bad Homburg (DE); Lida A. Quinchia Bustamante, Friedberg (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/759,310

(22) PCT Filed: Oct. 22, 2018

(86) PCT No.: PCT/EP2018/078904
§ 371 (c)(1),
(2) Date: Apr. 24, 2020

(87) PCT Pub. No.: WO2019/081435
PCT Pub. Date: May 2, 2019

(65) Prior Publication Data
US 2020/0297638 A1   Sep. 24, 2020

(30) Foreign Application Priority Data

Oct. 25, 2017  (EP) ..................................... 17198322

(51) Int. Cl.
*A61K 9/19* (2006.01)
*A61K 9/00* (2006.01)
(Continued)

(52) U.S. Cl.
CPC .............. *A61K 9/19* (2013.01); *A61K 9/0029* (2013.01); *A61K 31/07* (2013.01); *A61K 31/122* (2013.01);
(Continued)

(58) Field of Classification Search
None
See application file for complete search history.

(56) References Cited

U.S. PATENT DOCUMENTS

2003/0206969 A1* 11/2003 Nidamarty ............ A23L 33/175
424/648
2013/0224281 A1* 8/2013 Montesinos .......... A23L 33/105
424/450

FOREIGN PATENT DOCUMENTS

CN          104337829 A   *  2/2015
WO   WO-2011013138 A1  *  2/2011   ............. A23L 33/15

OTHER PUBLICATIONS

Machine translation, CN 104337829 A (Year: 2015).*
Partial written translation (tables), CN 104337829 A (Year: 2015).*

* cited by examiner

*Primary Examiner* — Bethany P Barham
*Assistant Examiner* — Barbara S Frazier
(74) *Attorney, Agent, or Firm* — HYLTON-RODIC LAW PLLC

(57) ABSTRACT

The invention relates to lyophilized products and reconstituted emulsions for parenteral application, which comprise all the 13 essential vitamins (A, D, E, K1, C, B1, B2, B3, B5, B6, B7, B9, and B12) in a single container, as well as to methods for preparing them.

14 Claims, 2 Drawing Sheets

(51) Int. Cl.
*A61K 9/107* (2006.01)
*A61K 31/07* (2006.01)
*A61K 31/122* (2006.01)
*A61K 31/197* (2006.01)
*A61K 31/355* (2006.01)
*A61K 31/375* (2006.01)
*A61K 31/4188* (2006.01)
*A61K 31/4415* (2006.01)
*A61K 31/455* (2006.01)
*A61K 31/51* (2006.01)
*A61K 31/525* (2006.01)
*A61K 31/593* (2006.01)
*A61K 31/714* (2006.01)
*A61K 47/44* (2017.01)

(52) U.S. Cl.
CPC .......... *A61K 31/197* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/593* (2013.01); *A61K 31/714* (2013.01); *A61K 47/44* (2013.01); *A61K 9/107* (2013.01)

ALL-IN-ONE LYOPHILIZED MULTIVITAMIN EMULSION FOR PARENTERAL APPLICATION

CROSS REFERENCE TO RELATED APPLICATIONS

This application is a U.S. National Stage Application of International Application No. PCT/EP2018/078904, filed Oct. 22, 2018, which claims the benefit of the filing date of European Application No. 17198322.4, filed Oct. 25, 2017, the contents of which are hereby incorporated by reference in their entirety.

FIELD OF THE INVENTION

The invention relates to multivitamin preparations for parenteral application. In particular, the invention relates to a lyophilized product and a reconstituted emulsion for parenteral application, to methods for preparing them, and to various uses thereof.

BACKGROUND OF THE INVENTION

Vitamins are required for specific metabolic functions. Vitamins are vital nutrients unable to be synthesized in the human body. Therefore, an adequate supply of vitamins is important, especially for patients in deficiency states. Vitamins can be classified according to their solubility characteristics. They can be water soluble or fat soluble.

The fat soluble vitamins, such as vitamin A, play an essential role in normal differentiation and maintenance of epithelial cells, development, reproduction and adequate immune function. However, its major role is related to vision improvement, as photoreceptor. Deficiency signs manifest first as night blindness followed by xerophthalmia and blindness. Vitamin E, on the other side, is a lipid soluble antioxidant, and its main role is to protect cell membrane polyunsaturated fatty acids from free radical oxidative damage. Vitamin D is required to maintain normal blood levels of calcium and phosphate, which are, in turn, needed for the normal mineralization of bones, muscle contraction, nerval conduction, and general cellular function in all cells of the body. Infants constitute a population at risk for vitamin D deficiency because of relatively large vitamin D needs brought about by their high rate of skeletal growth. However, adolescents and elderly people present this risk as well. The most important physiologic role of Vitamin K is the regulation of the coagulation factors. In addition, vitamin K plays a role in the synthesis of osteocalcin, a marker of bone formation.

Concerning the nine essential water soluble vitamins, Vitamin C, or ascorbic acid, is a cofactor in hydroxylation reactions in many biosynthetic processes, as well as an antioxidant. It is also involved in collagen metabolism. The classic clinical manifestation of vitamin C deficiency is scurvy. Thiamine, or vitamin $B_1$, is involved in carbohydrate metabolism as well as in lipid synthesis. Its requirements depend on carbohydrate intake. Thiamine deficiency may lead to beriberi with neurologic and cardiovascular symptoms. Riboflavin, or vitamin $B_2$, forms flavin adenine dinucleotides and thus participates in energy metabolism. The requirement for riboflavin is associated with protein intake. Clinical manifestations of deficiency include hyperemia of mucous membranes, stomatitis, dermatitis and anaemia. Vitamin $B_6$ (pyridoxine, pyridoxal and pyridoxamine) is involved in metabolism of amino acids, prostaglandins and carbohydrates, as well as in the development of the immune system and neurologic function. Pyridoxine deficiency manifests with hypochromic anaemia and neurologic symptoms. Vitamin $B_{12}$ is an organometallic complex. It participates in metabolic reactions involving the synthesis of DNA nucleotides. It is essential for normal blood formation and normal neurologic function. Niacin, or vitamin $B_3$, is essential for the synthesis of nicotinamide adenine dinucleotide and nicotinamide adenine dinucleotide phosphate, which serve as cofactors for electron transport and energy metabolism. Niacin deficiency causes pellagra, which involves cutaneous, gastrointestinal and neurologic symptoms. Vitamin $B_5$ is a precursor of coenzyme A and thus involved in many reactions of energy metabolism. Biotin, or vitamin $B_7$, functions as a coenzyme in bicarbonate-dependent carboxylation reactions. Biotin deficiency may result in dermatitis (red scaly rash around eyes, nose, and mouth), conjunctivitis, alopecia, and central nervous system abnormalities (such as depression). Vitamin $B_9$, or folic acid, is needed in the biosynthesis of purines and pyrimidines, in the metabolism of some amino acids, and in the catabolism of histidine.

Colloidal systems (e.g., emulsions) have been used as transport media for different active pharmaceutical ingredients (APIs), as those systems enhance the solubility of active pharmaceutical molecules and often minimize side effects. However, since these colloidal dispersions frequently have a water continuous phase, they are susceptible to microbial contamination, hydrolysis, degradation resulting from autoclaving, physicochemical instability and, eventually, loss of therapeutic activity.

Lyophilization of colloidal systems with an oil phase remains a huge challenge. Water is removed by sublimation; however, the presence of an oil phase poses several obstacles to this transport during the freeze-drying process. During freezing, mechanical stress is produced. Therefore, the contact of the crystallized water with the oil droplet surface can destabilize the system, provoking the release of the APIs present in the disperse phase (e.g., the oil phase) and thus the disruption of the pharmacological response. As a consequence, there are no freeze-dried multivitamin emulsions in the market.

Multivitamin products for parenteral application are commercially available. However, there is no product containing all the 13 essential vitamins in the physiologically required amounts in a single container (e.g., a single vial). Some multivitamin products do not contain Vitamin K. In other products the doses of the vitamins are not adequate. Furthermore, there are products where some of the vitamins are contained in a first compartment and the rest of the vitamins are contained in a second compartment and the contents of the two compartments are only mixed shortly before administration.

There is a general need for multivitamin preparations for parenteral application, which are stable, particularly storage stable, and convenient to use. In particular, there is a need for a stable product that contains all the 13 essential vitamins at requisite dosages in a single container.

SUMMARY OF THE INVENTION

The inventors found that a product containing all the 13 essential vitamins in a single container can be obtained by lyophilization of an emulsion. Accordingly, in one aspect of the invention there is provided a lyophilized product comprising in a single container:
15-100 mg of an oil component; and
the following vitamins:
a) 2970-3630 IU vitamin A;
b) 4.5-5.5 µg vitamin D (preferably vitamin D3);
c) 8.2-10.0 mg vitamin E;
d) 135-165 µg vitamin K1;
e) 202-248 mg vitamin C;
f) 5.4-6.6 mg vitamin B1;
g) 3.24-3.96 mg vitamin B2;
h) 5.4-6.6 mg vitamin B6;
i) 4.5-5.5 µg vitamin B12;
j) 0.54-0.66 mg vitamin B9;
k) 13.5-16.5 mg vitamin B5;
l) 54-66 ƒg vitamin B7; and
m) 36-44 mg vitamin B3.

The lyophilized product of the invention can be easily reconstituted. Accordingly, in a further aspect of the invention there is provided a reconstituted emulsion for parenteral application comprising in a single container:
15-100 mg of an oil component;
at least 2 ml of water; and
the following vitamins:
a) 2970-3630 IU vitamin A;
b) 4.5-5.5 µg vitamin D (preferably vitamin D3);
c) 8.2-10.0 mg vitamin E;
d) 135-165 µg vitamin K1;
e) 202-248 mg vitamin C;
f) 5.4-6.6 mg vitamin B1;
g) 3.24-3.96 mg vitamin B2;
h) 5.4-6.6 mg vitamin B6;
i) 4.5-5.5 µg vitamin B12;
j) 0.54-0.66 mg vitamin B9;
k) 13.5-16.5 mg vitamin B5;
l) 54-66 µg vitamin B7; and
m) 36-44 mg vitamin B3.

The doses of the vitamins in the lyophilized product of the invention and in the reconstituted emulsion of the invention are in accordance with the current ASPEN recommendations. The lyophilized product of the invention and the reconstituted emulsion of the invention are stable and easy to handle, transport and administer. In addition, the lyophilized product of the invention is storage stable; it can, for example, be stored at 25° C. for 52 weeks.

In further aspects of the invention there are provided methods for preparing the lyophilized product of the invention and the reconstituted emulsion of the invention. In further aspects of the invention there is provided the use of a lipid emulsion as a substrate for the preparation of a lyophilized product, wherein the lipid emulsion comprises 0.1-10 wt % of an oil component, based on the total weight of the lipid emulsion. Further aspects of the invention are described further below.

DETAILED DESCRIPTION OF THE INVENTION

Figure 1:
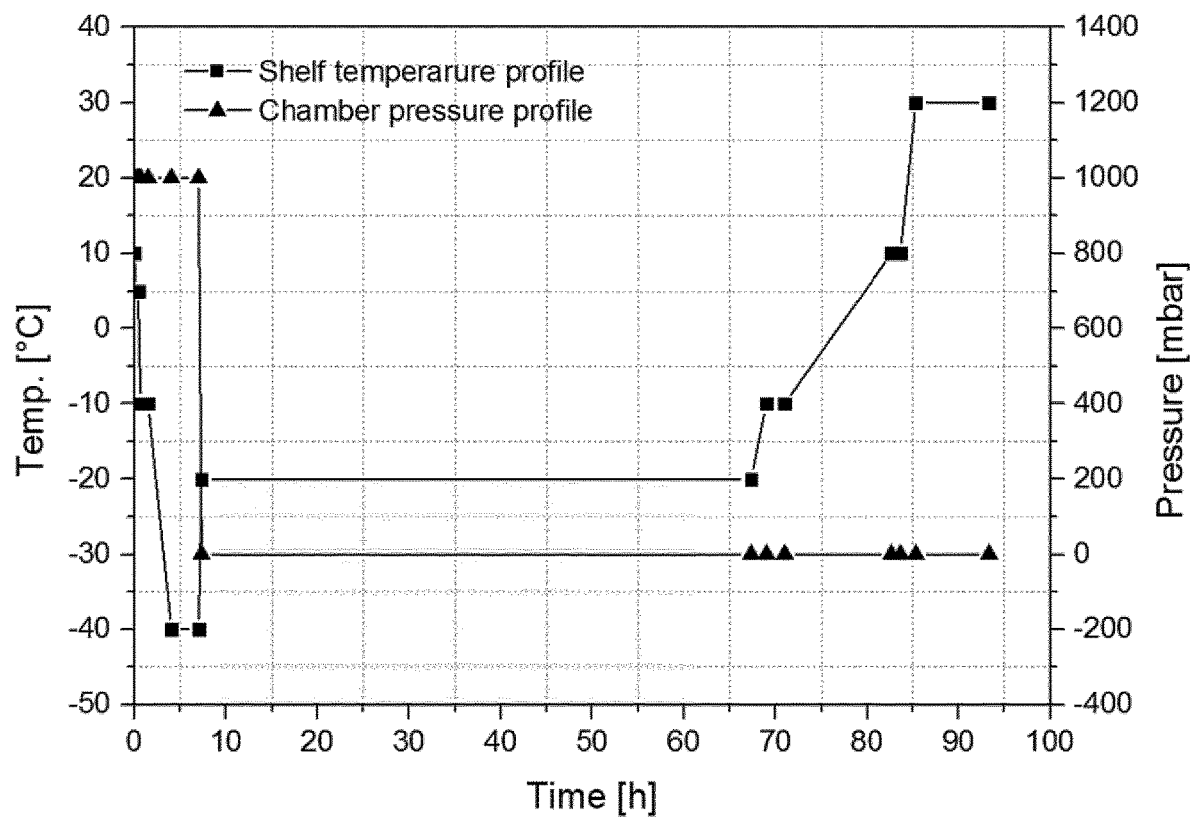
FIG. 1: Lyophilization protocol for the preparation of the lyophilized product described in Example 1 of the present application.

"All-in-One" is used herein to describe a product that contains all the 13 "essential vitamins" as active pharmaceuticals ingredients (APIs) in a single container.

"Lyophilized product" as used herein refers to a product, which is obtained after lyophilization of an emulsion, preferably after lyophilization of an oil-in-water (o/w) emulsion.

"Essential vitamins" as used herein refers to vitamins, which are recognized by the U.S. Food and Drug Administration (FDA), the American Medical Association (AMA), and the American Society of Parenteral and Enteral Nutrition (A.S.P.E.N) as necessary vitamins for the proper metabolic function of the human body. These vitamins include vitamin A, vitamin D (preferably vitamin D3), vitamin E, vitamin K1, vitamin C, vitamin B1, vitamin B2, vitamin B3, vitamin B5, vitamin B6, vitamin B7, vitamin B9, and vitamin B12. The term "lipo-soluble vitamins" as used herein refers to vitamin A, vitamin K1, vitamin D (preferably vitamin D3), and vitamin E.

The term "water-soluble vitamins" as used herein refers to vitamin B1, vitamin B2, vitamin B3, vitamin B5, vitamin B6, vitamin B7, vitamin B9, vitamin B12, and vitamin C.

"Lyophilization" as used herein refers to a process of removal of water by sublimation.

"Full Emulsion" as used herein refers to a lipid emulsion, which is obtained by mixing a "Base Emulsion" and a "water soluble vitamin solution" in a "mixing ratio". The Full Emulsion comprises an oil component, water (preferably water for injection), all the lipo-soluble vitamins (vitamin A, vitamin K1, vitamin D (preferably vitamin D3), and vitamin E), and all the water-soluble vitamins (vitamin B1, vitamin B2, vitamin B3, vitamin B5, vitamin B6, vitamin B7, vitamin B9, vitamin B12, and vitamin C). Preferably, the Full Emulsion further comprises an emulsifier (such as egg yolk phospholipids), a co-emulsifier (such as sodium oleate), and a lyoprotectant (such as trehalose). The Full Emulsion may also comprise a tonicity agent (such as glycerol). The Full Emulsion is the emulsion to be lyophilized.

"Base Emulsion" as used herein refers to a lipid emulsion, which comprises an oil component, water (preferably water for injection), and all the lipo-soluble vitamins (vitamin A, vitamin K1, vitamin D (preferably vitamin D3), and vitamin E). Preferably, the Base Emulsion further comprises an emulsifier (such as egg yolk phospholipids), a co-emulsifier (such as sodium oleate), and a lyoprotectant (such as trehalose). The Base Emulsion may also comprise a tonicity agent (such as glycerol).

"Water soluble vitamin solution" (herein referred to as WSVS) as used herein refers to a solution, which comprises water (preferably water for injection) and all the water-soluble vitamins (vitamin B1, vitamin B2, vitamin B3, vitamin B5, vitamin B6, vitamin B7, vitamin B9, vitamin B12, and vitamin C).

"Mixing ratio" as used herein refers to the ratio at which the "Base Emulsion" and the "water soluble vitamin solution" are mixed to obtain the "Full Emulsion".

"Reconstituted emulsion" as used herein refers to a product, which is obtained after reconstituting a lyophilized product, preferably the lyophilized product of the invention. The reconstituted emulsion of the invention is an oil-in-water (o/w) emulsion.

The expression "use of a lipid emulsion as a substrate" in the context of "use of a lipid emulsion as a substrate for the preparation of a lyophilized product" means that said lipid emulsion is what is lyophilized to prepare said lyophilized product.

Active Pharmaceutical Ingredients (APIs)

The lyophilized product of the invention and the reconstituted emulsion of the invention comprise as APIs all the 13 essential vitamins, which include vitamin A, vitamin D (preferably vitamin D3), vitamin E, vitamin K1, vitamin C, vitamin B1, vitamin B2, vitamin B3, vitamin B5, vitamin B6, vitamin B7, vitamin B9, and vitamin B12.

The lyophilized product of the invention and the reconstituted emulsion of the invention comprise in a single container 2970-3630 IU, preferably 3135-3465 IU, more preferably 3300 IU vitamin A. Vitamin A can be used in different forms. For example, vitamin A can be used in the form of retinol, retinyl esters, retinyl palmitate, retinyl acetate, or other derivatives of vitamin A. Particularly preferably, vitamin A is used in the form of retinyl palmitate.

The lyophilized product of the invention and the reconstituted emulsion of the invention comprise in a single container 4.5-5.5 µg, preferably 4.8-5.3 µg, more preferably 5.0 µg vitamin D (preferably vitamin D3). The term "vitamin D" as used herein refers to "vitamin D2" (ergocalciferol) and/or "vitamin D3" (cholecalciferol). Preferably, vitamin D3 is used. Vitamin D3 can be used in the form of cholecalciferol or derivatives thereof. If not specified otherwise, the amounts given herein for vitamin D3 refer to cholecalciferol. A person skilled in the art is aware that when vitamin D3 is used in a form other than cholecalciferol, the amounts need to be adapted (based on the molecular weight). Particularly preferably, vitamin D3 is used in the form of cholecalciferol.

The lyophilized product of the invention and the reconstituted emulsion of the invention comprise in a single container 8.2-10.0 mg, preferably 8.6-9.6 mg, more preferably 9.1 mg vitamin E. Vitamin E can be used in different forms. For example, vitamin E can be used in the form of alpha-DL-tocopherol, alpha-DL-tocopherol acetate, alpha-D-tocopherol, or other derivatives of vitamin E. If not specified otherwise, the amounts given herein for vitamin E refer to alpha-DL-tocopherol. A person skilled in the art is aware that when vitamin E is used in a form other than alpha-DL-tocopherol, the amounts need to be adapted (based on the molecular weight). Particularly preferably, vitamin E is used in the form of alpha-DL-tocopherol.

The lyophilized product of the invention and the reconstituted emulsion of the invention comprise in a single container 135-165 µg, preferably 143-158 µg, more preferably 150 µg vitamin K1. Vitamin K1 can be used in different forms. For example, vitamin K1 can be used in the form of phytomenadione or other derivatives of vitamin K1. If not specified otherwise, the amounts given herein for vitamin K1 refer to phytomenadione. A person skilled in the art is aware that when vitamin K1 is used in a form other than phytomenadione, the amounts need to be adapted (based on the molecular weight). Particularly preferably, vitamin K1 is used in the form of phytomenadione.

The lyophilized product of the invention and the reconstituted emulsion of the invention comprise in a single container 202-248 mg, preferably 214-236 mg, more preferably 225 mg vitamin C. Vitamin C can be used in different forms. For example, vitamin C can be used in the form of ascorbic acid, sodium ascorbate, magnesium ascorbate, ferrous ascorbate, or other derivatives of vitamin C. If not specified otherwise, the amounts given herein for vitamin C refer to sodium ascorbate. A person skilled in the art is aware that when vitamin C is used in a form other than sodium ascorbate, the amounts need to be adapted (based on the molecular weight). Particularly preferably, vitamin C is used in the form of sodium ascorbate.

The lyophilized product of the invention and the reconstituted emulsion of the invention comprise in a single container 5.4-6.6 mg, preferably 5.7-6.3 mg, more preferably 6 mg vitamin B1. Vitamin B1 can be used in different forms. For example, vitamin B1 can be used in the form of thiamine, thiamine hydrochloride, thiamine mononitrate, thiamine diphosphate, cocarboxylase tetrahydrate, or other derivatives of vitamin B1. If not specified otherwise, the amounts given herein for vitamin B1 refer to thiamine. A person skilled in the art is aware that when vitamin B1 is used in a form other than thiamine, the amounts need to be adapted (based on the molecular weight). Particularly preferably, vitamin B1 is used in the form of thiamine hydrochloride.

The lyophilized product of the invention and the reconstituted emulsion of the invention comprise in a single container 3.24-3.96 mg, preferably 3.4-3.8 mg, more preferably 3.6 mg vitamin B2. Vitamin B2 can be used in different forms. For example, vitamin B2 can be used in the form of riboflavin, riboflavin phosphates, riboflavin phosphate sodium salt, riboflavin phosphate sodium salt dihydrate, flavin mononucleotide, or other derivatives of vitamin B2. If not specified otherwise, the amounts given herein for vitamin B2 refer to riboflavin. A person skilled in the art is aware that when vitamin B2 is used in a form other than riboflavin, the amounts need to be adapted (based on the molecular weight). Particularly preferably, vitamin B2 is used in the form of riboflavin phosphate sodium salt (preferably riboflavin phosphate sodium salt dihydrate).

The lyophilized product of the invention and the reconstituted emulsion of the invention comprise in a single container 36-44 mg, preferably 38-42 mg, more preferably 40 mg vitamin B3. Vitamin B3 can be used in different forms. For example, vitamin B3 can be used in the form of niacin (nicotinic acid), niacinamide (nicotinamide), nicotinate, nicotinic acid hydrochloride, or other derivatives of vitamin B3. If not specified otherwise, the amounts given herein for vitamin B3 refer to niacin. A person skilled in the art is aware that when vitamin B3 is used in a form other than niacin, the amounts need to be adapted (based on the molecular weight). Particularly preferably, vitamin B3 is used in the form of niacin.

The lyophilized product of the invention and the reconstituted emulsion of the invention comprise in a single container 13.5-16.5 mg, preferably 14-16 mg, more preferably 15 mg vitamin B5. Vitamin B5 can be used in different forms. For example, vitamin B5 can be used in the form of pantothenic acid, dexpanthenol, sodium pantothenate, calcium pantothenate, zinc pantothenate, or other derivatives of vitamin B5. If not specified otherwise, the amounts given herein for vitamin B5 refer to pantothenic acid. A person skilled in the art is aware that when vitamin B5 is used in a form other than pantothenic acid, the amounts need to be adapted (based on the molecular weight). Particularly preferably, vitamin B5 is used in the form of dexpanthenol.

The lyophilized product of the invention and the reconstituted emulsion of the invention comprise in a single container 5.4-6.6 mg, preferably 5.7-6.3 mg, more preferably 6 mg vitamin B6. Vitamin B6 can be used in different forms. For example, vitamin B6 can be used in the form of pyridoxine, pyridoxine hydrochloride, pyridoxal, pyridoxamine, or other derivatives of vitamin B6. If not specified otherwise, the amounts given herein for vitamin B6 refer to pyridoxine. A person skilled in the art is aware that when vitamin B6 is used in a form other than pyridoxine, the amounts need to be adapted (based on the molecular weight). Particularly preferably, vitamin B6 is used in the form of pyridoxine hydrochloride.

The lyophilized product of the invention and the reconstituted emulsion of the invention comprise in a single container 54-66 µg, preferably 57-63 µg, more preferably 60 µg vitamin B7. Vitamin B7 can be used in different forms.

For example, vitamin B7 can be used in the form of biotin or derivatives thereof. If not specified otherwise, the amounts given herein for vitamin B7 refer to biotin. A person skilled in the art is aware that when vitamin B7 is used in a form other than biotin, the amounts need to be adapted (based on the molecular weight). Particularly preferably, vitamin B7 is used in the form of biotin.

The lyophilized product of the invention and the reconstituted emulsion of the invention comprise in a single container 0.54-0.66 mg, preferably 0.57-0.63 mg, more preferably 0.60 mg vitamin B9. Vitamin B9 can be used in different forms. For example, vitamin B9 can be used in the form of folate, folic acid, folic acid potassium salt, or other derivatives of vitamin B9. If not specified otherwise, the amounts given herein for vitamin B9 refer to folic acid. A person skilled in the art is aware that when vitamin B9 is used in a form other than folic acid, the amounts need to be adapted (based on the molecular weight). Particularly preferably, vitamin B9 is used in the form of folic acid.

The lyophilized product of the invention and the reconstituted emulsion of the invention comprise in a single container 4.5-5.5 µg, preferably 4.8-5.3 µg, more preferably 5 µg vitamin B12. Vitamin B12 can be used in different forms. For example, vitamin B12 can be used in the form of cyanocobalamin, methylcobalamin, adenosylcobalamin, or other derivatives of vitamin B12. If not specified otherwise, the amounts given herein for vitamin B12 refer to cyanocobalamin. A person skilled in the art is aware that when vitamin B12 is used in a form other than cyanocobalamin, the amounts need to be adapted (based on the molecular weight). Particularly preferably, vitamin B12 is used in the form of cyanocobalamine.

In particularly preferred embodiments, vitamin A is used in the form of retinyl palmitate; vitamin D (preferably vitamin D3) is used in the form of cholecalciferol; vitamin E is used in the form of alpha-DL-tocopherol; vitamin K1 is used in the form of phytomenadione; vitamin C is used in the form of sodium ascorbate; vitamin B1 is used in the form of thiamine hydrochloride; vitamin B2 is used in the form of riboflavin phosphate sodium salt (preferably riboflavin phosphate sodium salt dihydrate); vitamin B6 is used in the form of pyridoxine hydrochloride; vitamin B12 is used in the form of cyanocobalamine; vitamin B9 is used in the form of folic acid; vitamin B5 is used in the form of dexpanthenol; vitamin B7 is used in the form of biotin; and vitamin B3 is used in the form of niacin.

These particularly preferred vitamin forms are particularly suitable (also in combination with each other) for the lyophilization, the reconstitution, and the administration.

Excipients

The lyophilized product of the invention and the reconstituted emulsion of the invention comprise an oil component as an excipient. The oil component serves as a solvent for the lipo-soluble vitamins. Optionally, the lyophilized product of the invention and the reconstituted emulsion of the invention comprise further excipients, which include, for example, a tonicity agent, an emulsifier, a co-emulsifier, and/or a lyoprotectant. The reconstituted emulsion of the invention comprises water as an excipient. Water serves as a solvent for the water soluble vitamins and, if present, the excipients. Optionally, the lyophilized product of the invention and the reconstituted emulsion of the invention further comprise a base and/or an acid, which can be used for pH-adjustment.

In preferred embodiments, the lyophilized product of the invention and the reconstituted emulsion of the invention comprise an emulsifier, a co-emulsifier, and a lyoprotectant.

In other preferred embodiments, the lyophilized product of the invention and the reconstituted emulsion of the invention comprise a tonicity agent, an emulsifier, a co-emulsifier, and a lyoprotectant.

The particularly preferred excipients mentioned herein (e.g., soybean oil, egg yolk phospholipids, oleic acid or sodium oleate, trehalose, with or without glycerol) are particularly suitable (also in combination with each other) for the lyophilization, the reconstitution, and the administration.

Oil Component

The lyophilized product of the invention and the reconstituted emulsion of the invention comprise an oil component. Suitable oils are known to a person skilled in the art.

Preferably, the oil component comprises soybean oil, olive oil, fish oil, fish oil extract, cottonseed oil, safflower oil, corn oil, sunflower oil, coconut oil, palm kernel oil, rapeseed oil, medium chain triglycerides (MCT), or mixtures thereof. More preferably, the oil component comprises soybean oil, olive oil, fish oil, sunflower oil, MCT, or mixtures thereof. Particularly preferably, the oil component comprises soybean oil.

The amount of the oil component in the lyophilized product of the invention and in the reconstituted emulsion of the invention in a single container is, for example, 15-100 mg, preferably 30-80 mg, more preferably 40-60 mg.

Tonicity Agent

Optionally, the lyophilized product of the invention and the reconstituted emulsion of the invention further comprise a tonicity agent. Suitable tonicity agents are known to a person skilled in the art.

Preferred tonicity agents are glycerol, propylene glycol, sorbitol, mannitol, dextrose, lactose, or sodium chloride. More preferred tonicity agents are glycerol, propylene glycol, or sodium chloride. A particularly preferred tonicity agent is glycerol.

For example, the amount of the tonicity agent in the lyophilized product of the invention and in the reconstituted emulsion of the invention in a single container is 0-180 mg, preferably 0-150 mg, more preferably 0-130 mg.

If present, the amount of the tonicity agent in the lyophilized product of the invention and in the reconstituted emulsion of the invention in a single container is, for example, 10-180 mg, preferably 50-150 mg, more preferably 90-130 mg.

Emulsifier

Preferably, the lyophilized product of the invention and the reconstituted emulsion of the invention further comprise an emulsifier. Suitable emulsifiers are known to a person skilled in the art.

Preferred emulsifiers are phospholipids. More preferred emulsifiers are egg yolk phospholipids or soybean phospholipids. Particular preference is given to egg yolk phospholipids.

Egg yolk phospholipids are commercially available, for example under the trade name PL 90 or Lipoid E80. Soybean phospholipids are commercially available, for example under the trade name Epikurin™ 170.

If present, the amount of the emulsifier in the lyophilized product of the invention and in the reconstituted emulsion of the invention in a single container is, for example, 10-120 mg, preferably 20-100 mg, more preferably 40-80 mg.

Co-Emulsifier

Preferably, the lyophilized product of the invention and the reconstituted emulsion of the invention further comprise a co-emulsifier. Suitable co-emulsifiers are known to a person skilled in the art.

Preferred co-emulsifiers are fatty acids or salts of fatty acids. More preferred co-emulsifiers are salts of fatty acids. Particular preference is given to oleic acid or sodium oleate. Very particular preference is given to sodium oleate.

If present, the amount of the co-emulsifier in the lyophilized product of the invention and in the reconstituted emulsion of the invention in a single container is, for example, 0.5-4.0 mg, preferably 1.0-2.0 mg, more preferably 1.2-1.8 mg.

Lyoprotectant

Preferably, the lyophilized product of the invention and the reconstituted emulsion of the invention further comprise a lyoprotectant. Suitable lyoprotectants are known to a person skilled in the art.

Preferred lyoprotectants are sugars. More preferred lyoprotectants are monosaccharides or disaccharides. Even more preferred lyoprotectants are trehalose, mannitol, sucrose, lactose, maltose, or glucose. A particularly preferred lyoprotectant is trehalose.

If present, the amount of the lyoprotectant in the lyophilized product of the invention and in the reconstituted emulsion of the invention in a single container is, for example, 150-1000 mg, preferably 300-800 mg, more preferably 400-600 mg.

Water

The lyophilized product of the invention may comprise water. Particular preference is given to water for injection (WFI).

If present, the amount of water in the lyophilized product of the invention is, for example, less than 5 wt %, preferably less than 3 wt %, more preferably less than 2 wt %, even more preferably less than 1.5 wt %, particularly preferably less than 1 wt %, based on the total weight of the lyophilized product.

The reconstituted emulsion of the invention comprises water. Particular preference is given to water for injection (WFI).

The amount of water in the reconstituted emulsion of the invention is at least 2 mL, preferably at least 3 mL, more preferably at least 5 mL, even more preferably at least 9 mL, even more preferably at least 10 mL.

The amount of water in the reconstituted emulsion of the invention is, for example, 2-20 ml, preferably 3-18 ml, more preferably 5-15 ml, even more preferably 8-12 ml, even more preferably 9-11 ml, particularly preferably 10 ml.

pH Adjustment

Optionally, the lyophilized product of the invention and the reconstituted emulsion of the invention further comprise a base, such as sodium hydroxide (NaOH). A base, such as sodium hydroxide, can, for example, be used for pH adjustment. Optionally, the lyophilized product of the invention and the reconstituted emulsion of the invention further comprise an acid, such as hydrochloric acid (HCl). An acid, such as hydrochloric acid, can, for example, be used for pH adjustment.

Container

The lyophilized product of the invention comprises in a single container: an oil component, vitamin A, vitamin D, vitamin E, vitamin K1, vitamin C, vitamin B1, vitamin B2, vitamin B6, vitamin B12, vitamin B9, vitamin B5, vitamin B7, and vitamin B3.

If the lyophilized product of the invention comprises further components (such as the ones mentioned herein), these further components are comprised in the same container as the oil component and the vitamins.

To give a few examples: If the lyophilized product of the invention further comprises a tonicity agent, the tonicity agent is comprised in the same container as the oil component and the vitamins. If the lyophilized product of the invention further comprises an emulsifier, the emulsifier is comprised in the same container as the oil component and the vitamins. If the lyophilized product of the invention further comprises a co-emulsifier, the co-emulsifier is comprised in the same container as the oil component and the vitamins. If the lyophilized product of the invention further comprises a lyoprotectant, the lyoprotectant is comprised in the same container as the oil component and the vitamins.

The reconstituted emulsion of the invention comprises in a single container: an oil component, water, vitamin A, vitamin D, vitamin E, vitamin K1, vitamin C, vitamin B1, vitamin B2, vitamin B6, vitamin B12, vitamin B9, vitamin B5, vitamin B7, and vitamin B3.

If the reconstituted emulsion of the invention comprises further components (such as the ones mentioned herein), these further components are comprised in the same container as the oil component, the water, and the vitamins.

To give a few examples: If the reconstituted emulsion of the invention further comprises a tonicity agent, the tonicity agent is comprised in the same container as the oil component, the water, and the vitamins. If the reconstituted emulsion of the invention further comprises an emulsifier, the emulsifier is comprised in the same container as the oil component, the water, and the vitamins. If the reconstituted emulsion of the invention further comprises a co-emulsifier, the co-emulsifier is comprised in the same container as the oil component, the water, and the vitamins. If the reconstituted emulsion of the invention further comprises a lyoprotectant, the lyoprotectant is comprised in the same container as the oil component, the water, and the vitamins.

Preferred containers are vials, bottles, or ampoules. More preferred containers are vials or bottles. Even more preferred containers are vials. Also even more preferred containers are bottles.

Particular preference is given to glass containers. Accordingly, preferred containers are glass vials, glass bottles, or glass ampoules. More preferred containers are glass vials or glass bottles. Even more preferred containers are glass vials. Also even more preferred containers are glass bottles.

Typically, the container has a volume of 5-20 mL, preferably 5-15 mL, more preferably 8-15 mL, even more preferably 8-12 mL, particularly preferably 10 mL. Particular preference is given to 10 mL glass vials (i.e. glass vials having a volume of 10 mL) or 10 mL glass bottles (i.e. glass bottles having a volume of 10 mL). Very particular preference is given to 10 mL glass vials.

In a further aspect of the invention there is provided a container comprising a lyophilized product as defined herein. In a preferred embodiment there is provided a glass container comprising a lyophilized product as defined herein. In a particularly preferred embodiment there is provided a glass vial comprising a lyophilized product as defined herein. In another particularly preferred embodiment there is provided a glass bottle comprising a lyophilized product as defined herein.

In a further aspect of the invention there is provided a container comprising a reconstituted emulsion as defined herein. In a preferred embodiment there is provided a glass container comprising a reconstituted emulsion as defined herein. In a particularly preferred embodiment there is provided a glass vial comprising a reconstituted emulsion as defined herein. In another particularly preferred embodiment there is provided a glass bottle comprising a reconstituted emulsion as defined herein.

Preparation

In one aspect of the invention there is provided a method for preparing a lyophilized product as defined herein, which method comprises:
- a1) preparing a water soluble vitamin solution (WSVS) comprising water, vitamin C, vitamin B1, vitamin B2, vitamin B6, vitamin B12, vitamin B9, vitamin B5, vitamin B7, and vitamin B3;
- a2) sterilizing the water soluble vitamin solution prepared in step a1) to obtain a sterilized water soluble vitamin solution;
- a3) preparing a Base Emulsion comprising the oil component, vitamin A, vitamin D (preferably vitamin D3), vitamin E, and vitamin K1;
- a4) sterilizing the Base Emulsion prepared in step a3) to obtain a sterilized Base Emulsion;
- a5) combining the sterilized water soluble vitamin solution obtained in step a2) and the sterilized Base Emulsion obtained in step a4) to obtain a Full Emulsion;
- a6) lyophilizing the Full Emulsion obtained in step a5) to obtain the lyophilized product.

In another aspect of the invention there is provided a method for preparing a reconstituted emulsion as defined herein, which method comprises:
- a1) preparing a water soluble vitamin solution (WSVS) comprising water, vitamin C, vitamin B1, vitamin B2, vitamin B6, vitamin B12, vitamin B9, vitamin B5, vitamin B7, and vitamin B3;
- a2) sterilizing the water soluble vitamin solution prepared in step a1) to obtain a sterilized water soluble vitamin solution;
- a3) preparing a Base Emulsion comprising the oil component, vitamin A, vitamin D (preferably vitamin D3), vitamin E, and vitamin K1;
- a4) sterilizing the Base Emulsion prepared in step a3) to obtain a sterilized Base Emulsion;
- a5) combining the sterilized water soluble vitamin solution obtained in step a2) and the sterilized Base Emulsion obtained in step a4) to obtain a Full Emulsion;
- a6) lyophilizing the Full Emulsion obtained in step a5) to obtain a lyophilized product;
- a7) adding water to the lyophilized product obtained in step a6) to obtain the reconstituted emulsion.

According to step a1) of the method for preparing a lyophilized product and step a1) of the method for preparing a reconstituted emulsion, a water soluble vitamin solution (herein referred to as WSVS) comprising water, vitamin C, vitamin B1, vitamin B2, vitamin B6, vitamin B12, vitamin B9, vitamin B5, vitamin B7, and vitamin B3 is prepared.

Particularly preferably, water for injection (WFI) is used to prepare the water soluble vitamin solution of step a1).

The amounts of the components of the water soluble vitamin solution of step a1) are chosen such that the lyophilized product to be prepared or the reconstituted emulsion to be prepared is obtained.

Typically, the amounts of the components of the water soluble vitamin solution of step a1) depend on the ratio at which the sterilized Base Emulsion obtained in step a4) and the sterilized water soluble vitamin solution obtained in step a2) are mixed to obtain the Full Emulsion of step a5), herein referred to as the mixing ratio.

Typically, the ratio of all the water-soluble vitamins to each other in the water soluble vitamin solution of step a1) corresponds to the ratio of all the water-soluble vitamins to each other in the lyophilized product to be prepared or in the reconstituted emulsion to be prepared.

The WSVS can, in some embodiments, have a composition as given in Table 1.

TABLE 1

| Raw material | Concentration in [wt %] |
|---|---|
| Vitamin B1 in the form of thiamine hydrochloride | 0.57-0.69 |
| Vitamin B2 in the form of riboflavin phosphate sodium salt dihydrate | 0.34-0.41 |
| Vitamin B3 in the form of niacin | 2.88-3.52 |
| Vitamin B5 in the form of dexpanthenol | 1.03-1.26 |
| Vitamin B6 in the form of pyridoxine hydrochloride | 0.53-0.64 |
| Vitamin B7 in the form of biotin | 0.0043-0.0053 |
| Vitamin B9 in the form of folic acid | 0.047-0.057 |
| Vitamin B12 in the form of cyanocobalamine | 0.00038-0.00046 |
| Vitamin C in the form of sodium ascorbate | 16.41-20.06 |
| Water for injection | to 100 |

Preferably, the water soluble vitamin solution prepared according to step a1) has a pH of 4.0-7.0, more preferably 4.5-6.5, particularly preferably 5.0-6.0. Also preferably, the water soluble vitamin solution prepared according to step a1) has a pH of 6.0-8.0, more preferably 6.0-7.5, particularly preferably 6.0-7.0, also particularly preferably 7.0-7.5.

Preferably, the water soluble vitamin solution of step a1) is prepared by adding vitamin C, vitamin B1, vitamin B2, vitamin B6, vitamin B12, vitamin B9, vitamin B5, vitamin B7, and vitamin B3 to water.

More preferably, vitamin B1, vitamin B2, vitamin B6, vitamin B9, vitamin B5, vitamin B7, and vitamin B3 are added to water; then vitamin C is added; and then vitamin B12 is added. Even more preferably, vitamin B1, vitamin B2, vitamin B6, vitamin B9, vitamin B5, vitamin B7, and vitamin B3 are added to water at a temperature of 20-60° C., preferably 30-50° C., particularly preferably 40-45° C.; the resulting mixture is allowed to become homogeneous, for example by stirring; then vitamin C is added; the resulting mixture is allowed to reach a temperature of 10-20° C., particularly preferably 10-15° C., for example by stirring; and then vitamin B12 is added.

The water soluble vitamin solution of step a1) can be prepared on any scale, e.g. a 100 mL scale, a 1 liter scale, a 10 liter scale, or a 100 liter scale. For example, the WSVS can be prepared on a 1-5 liter scale, e.g. a 1-3 liter scale. To give another example, the WSVS can be prepared on a 10-100 liter scale, e.g. a 30-50 liter scale. To give a further example, the WSVS can be prepared on a 100-500 liter scale, e.g. a 100-200 liter scale.

According to step a2) of the method for preparing a lyophilized product and step a2) of the method for preparing a reconstituted emulsion, the water soluble vitamin solution prepared in step a1) is sterilized to obtain a sterilized water soluble vitamin solution.

Preferably, the water soluble vitamin solution prepared in step a1) is sterilized by sterile filtration. The sterile filtration can, for example, be carried out using filters having pore sizes of 0.04-0.45 μm, preferably 0.1-0.3 μm, more preferably 0.1-0.2 μm, also more preferably 0.15-0.25 μm, particularly preferably 0.2 μm.

According to step a3) of the method for preparing a lyophilized product and step a3) of the method for preparing a reconstituted emulsion, a Base Emulsion comprising the oil component, vitamin A, vitamin D (preferably vitamin D3), vitamin E, and vitamin K1 is prepared.

Particularly preferably, water for injection (WFI) is used to prepare the Base Emulsion of step a3).

The amounts of the components of the Base Emulsion of step a3) are chosen such that the lyophilized product to be prepared or the reconstituted emulsion to be prepared is obtained.

Typically, the amounts of the components of the Base Emulsion of step a3) depend on the ratio at which the sterilized Base Emulsion obtained in step a4) and the sterilized water soluble vitamin solution obtained in step a2) are mixed to obtain the Full Emulsion of step a5), herein referred to as the mixing ratio.

Typically, the ratio of all the lipo-soluble vitamins to each other in the Base Emulsion of step a3) corresponds to the ratio of all the lipo-soluble vitamins to each other in the lyophilized product to be prepared or in the reconstituted emulsion to be prepared.

Typically, the ratio of the oil component to each of the lipo-soluble vitamins in the Base Emulsion of step a3) corresponds to the ratio of the oil component to each of the lipo-soluble vitamins in the lyophilized product to be prepared or in the reconstituted emulsion to be prepared.

The Base Emulsion can, in some embodiments, have a composition as given in Table 2a.

TABLE 2a

| Raw material | Concentration in [wt %] |
| --- | --- |
| Vitamin A in the form of retinyl palmitate | 0.045-0.055 |
| Vitamin D3 in the form of cholecalciferol | 0.00012-0.00014 |
| Vitamin E in the form of alpha-DL-tocopherol | 0.23-0.28 |
| Vitamin K1 in the form of phytomenadione | 0.0036-0.0044 |
| Oil (e.g., soybean oil) | 1.0-3.0, preferably 1.0-2.0 |
| Tonicity agent (e.g., glycerol) | 0-2.7, preferably 2.0-2.5 |
| Emulsifier (e.g., egg yolk phospholipids) | 0.3-1.9, preferably 1.4-1.8 |
| Co-emulsifier (e.g., sodium oleate) | 0-0.06, preferably 0.03-0.05 |
| Lyoprotectant (e.g., trehalose) | 4.0-16.0, preferably 12.0-14.7 |
| Water for injection | to 100 |

The Base Emulsion can, in some embodiments, have a composition as given in Table 2b.

TABLE 2b

| Raw material | Concentration in [wt %] |
| --- | --- |
| Vitamin A in the form of retinyl palmitate | 0.045-0.055 |
| Vitamin D3 in the form of cholecalciferol | 0.00012-0.00014 |
| Vitamin E in the form of alpha-DL-tocopherol | 0.23-0.28 |
| Vitamin K1 in the form of phytomenadione | 0.0036-0.0044 |
| Oil (e.g., soybean oil) | 1.0-3.0, preferably 1.0-2.0 |
| Emulsifier (e.g., egg yolk phospholipids) | 0.3-1.9, preferably 1.4-1.8 |
| Co-emulsifier (e.g., sodium oleate) | 0-0.06, preferably 0.03-0.05 |
| Lyoprotectant (e.g., trehalose) | 4.0-16.0, preferably 12.0-14.7 |
| Water for injection | to 100 |

Preferably, the Base Emulsion prepared according to step a3) has a pH of 7.0-9.5, more preferably 7.5-9.0, particularly preferably 8.0-8.5.

Preferably, the Base Emulsion of step a3) is prepared by mixing and homogenization. More preferably, the Base Emulsion of step a3) is prepared by mixing the oil component, vitamin A, vitamin D, vitamin E, and vitamin K1 with water and, if present, one or more of a tonicity agent, an emulsifier, a co-emulsifier, and/or a lyoprotectant (preferably an emulsifier, a co-emulsifier, and a lyoprotectant); followed by homogenization. Also more preferably, the Base Emulsion of step a3) is prepared by mixing an oil phase which contains the oil component, vitamin A, vitamin D, vitamin E, and vitamin K1 with a water phase which contains water and, if present, one or more of a tonicity agent, an emulsifier, a co-emulsifier, and/or a lyoprotectant (preferably an emulsifier, a co-emulsifier, and a lyoprotectant); followed by homogenization.

Mixing is preferably carried out at a temperature of 50-80° C., more preferably 55-75° C., even more preferably 60-70° C., particularly preferably 60-65° C.

Even more preferably, the oil component, vitamin A, vitamin D, vitamin E, and vitamin K1 are premixed. Also even more preferably, water and, if present, one or more of a tonicity agent, an emulsifier, a co-emulsifier, and/or a lyoprotectant (preferably an emulsifier, a co-emulsifier, and a lyoprotectant) are premixed.

Particularly preferably, the oil component, vitamin A, vitamin D, vitamin E, and vitamin K1 are premixed at a temperature of 50-80° C., preferably 55-75° C., more preferably 60-70° C., particularly preferably 60-65° C.; and water and, if present, one or more of a tonicity agent, an emulsifier, a co-emulsifier, and/or a lyoprotectant (preferably an emulsifier, a co-emulsifier, and a lyoprotectant) are premixed at a temperature of 50-80° C., preferably 55-75° C., more preferably 60-70° C., particularly preferably 60-65° C.

Homogenization is preferably carried out at a temperature of 45-70° C., more preferably 50-65° C., even more preferably 55-65° C., particularly preferably 55-60° C.

Homogenization can, for example, be carried out at a pressure of 300-700 bar, more preferably 400-600 bar, even more preferably 450-550 bar, particularly preferably 500 bar.

Homogenization is preferably carried out in two stages; in the first stage the pressure is preferably 400-600 bar, more preferably 450-550 bar, particularly preferably 500 bar; in the second stage the pressure is preferably 40-60 bar, more preferably 45-55 bar, particularly preferably 50 bar.

Homogenization is preferably carried out in cycles. 4, 5 or 6 cycles of homogenization are particularly preferred.

If the lyophilized product of the invention and the reconstituted emulsion of the invention further comprise a tonicity agent, the tonicity agent is preferably added in step a3) of the method for preparing a lyophilized product and step a3) of the method for preparing a reconstituted emulsion. Accordingly, in some embodiments the Base Emulsion prepared according to step a3) further comprises a tonicity agent.

If present, the ratio of the tonicity agent to each of the lipo-soluble vitamins in the Base Emulsion of step a3) typically corresponds to the ratio of the tonicity agent to each of the lipo-soluble vitamins in the lyophilized product to be prepared or in the reconstituted emulsion to be prepared.

If the lyophilized product of the invention and the reconstituted emulsion of the invention further comprise an emulsifier, the emulsifier is preferably added in step a3) of the method for preparing a lyophilized product and step a3) of the method for preparing a reconstituted emulsion. Accordingly, in preferred embodiments the Base Emulsion prepared according to step a3) further comprises an emulsifier.

If present, the ratio of the emulsifier to each of the lipo-soluble vitamins in the Base Emulsion of step a3) typically corresponds to the ratio of the emulsifier to each of the lipo-soluble vitamins in the lyophilized product to be prepared or in the reconstituted emulsion to be prepared.

If the lyophilized product of the invention and the reconstituted emulsion of the invention further comprise a co-emulsifier, the co-emulsifier is preferably added in step a3) of the method for preparing a lyophilized product and step a3) of the method for preparing a reconstituted emulsion. Accordingly, in preferred embodiments the Base Emulsion prepared according to step a3) further comprises a co-emulsifier.

If present, the ratio of the co-emulsifier to each of the lipo-soluble vitamins in the Base Emulsion of step a3) typically corresponds to the ratio of the co-emulsifier to each of the lipo-soluble vitamins in the lyophilized product to be prepared or in the reconstituted emulsion to be prepared.

If the lyophilized product of the invention and the reconstituted emulsion of the invention further comprise a lyoprotectant, the lyoprotectant is preferably added in step a3) of the method for preparing a lyophilized product and step a3) of the method for preparing a reconstituted emulsion. Accordingly, in preferred embodiments the Base Emulsion prepared according to step a3) further comprises a lyoprotectant.

If present, the ratio of the lyoprotectant to each of the lipo-soluble vitamins in the Base Emulsion of step a3) typically corresponds to the ratio of the lyoprotectant to each of the lipo-soluble vitamins in the lyophilized product to be prepared or in the reconstituted emulsion to be prepared.

The Base Emulsion of step a3) can be prepared on any scale, e.g. a 100 mL scale, a 1 liter scale, a 10 liter scale, or a 100 liter scale. For example, the Base Emulsion can be prepared on a 1-5 liter scale, e.g. a 1-3 liter scale. To give another example, the Base Emulsion can be prepared on a 10-100 liter scale, e.g. a 30-50 liter scale. To give a further example, the Base Emulsion can be prepared on a 100-500 liter scale, e.g. a 100-200 liter scale.

According to step a4) of the method for preparing a lyophilized product and step a4) of the method for preparing a reconstituted emulsion, the Base Emulsion prepared in step a3) is sterilized to obtain a sterilized Base Emulsion.

Preferably, the Base Emulsion prepared in step a3) is sterilized by ultra-high temperature (UHT) sterilization. The ultra-high temperature (UHT) sterilization can, for example, be carried out at 140° C. for 9 seconds.

According to step a5) of the method for preparing a lyophilized product and step a5) of the method for preparing a reconstituted emulsion, the sterilized water soluble vitamin solution obtained in step a2) and the sterilized Base Emulsion obtained in step a4) are combined to obtain a Full Emulsion.

Preferably, the sterilized Base Emulsion obtained in step a4) and the sterilized water soluble vitamin solution obtained in step a2) are mixed in a preferred mixing ratio to obtain the Full Emulsion of step a5).

Preferably, the mixing ratio (weight ratio) of the sterilized Base Emulsion obtained in step a4) to the sterilized water soluble vitamin solution obtained in step a2) is from 1.5-4.5:1, more preferably 2-4:1, even more preferably 2.5-3.5:1, particularly preferably 3:1.

These preferred mixing ratios warrant a good solubility of the water soluble vitamins on the one hand and requisite lipid emulsion properties of the Full Emulsion on the other hand. For example, the obtained lipid emulsion is homogeneous, easy to handle, stable, and particularly suitable for the lyophilization.

Typically, the ratio of all components of the Full Emulsion of step a5), except water, to each other (i.e. the ratio of all vitamins, the oil component, and all optional excipients to each other) in the Full Emulsion of step a5) corresponds to the ratio of these components to each other in the lyophilized product to be prepared or in the reconstituted emulsion to be prepared.

The amount of the oil component in the Full Emulsion of step a5) is, for example, 0.1-10 wt %, preferably, 0.2-5 wt %, more preferably 0.5-3 wt %, even more preferably 0.5-2.5 wt %, particularly preferably 0.5-1.5 wt %, also particularly preferably 1-2 wt %, also particularly preferably 2.0-2.5 wt %, based on the total weight of the Full Emulsion of step a5). In particularly preferred embodiments, the amount of the oil component in the Full Emulsion of step a5) is 1 wt %, based on the total weight of the Full Emulsion of step a5).

Preferably, the amount of all components of the Full Emulsion of step a5), except water, (i.e. the amount of all vitamins, the oil component. and all optional excipients) in the Full Emulsion of step a5) is 170-200 mg/mL, more preferably 175-195 mg/mL, even more preferably 180-190 mg/mL, particularly preferably 185 mg/mL. In this context, "/mL" (per mL) means per mL of the Full Emulsion.

The sterilized water soluble vitamin solution obtained in step a2) and the sterilized Base Emulsion obtained in step a4) are preferably combined at a temperature of 5-25° C., more preferably 5-20° C., even more preferably 10-20° C., particularly preferably 10-15° C.

Preferably, the sterilized water soluble vitamin solution obtained in step a2) and the sterilized Base Emulsion obtained in step a4) are combined under aseptic conditions.

The Full Emulsion obtained in step a5) preferably has a pH of 6.0-9.0, more preferably 6.0-8.0, even more preferably 7.0-8.0, particularly preferably 7.0-7.5.

The Full Emulsion of step a5) can be prepared on any scale, e.g. a 100 mL scale, a 1 liter scale, a 10 liter scale, or a 100 liter scale. For example, the Full Emulsion can be prepared on a 1-5 liter scale, e.g. a 1-3 liter scale. To give another example, the Full Emulsion can be prepared on a 10-100 liter scale, e.g. a 30-50 liter scale. To give a further example, the Full Emulsion can be prepared on a 100-500 liter scale, e.g. a 100-200 liter scale.

According to step a6) of the method for preparing a lyophilized product and step a6) of the method for preparing a reconstituted emulsion, the Full Emulsion obtained in step a5) is lyophilized to obtain the/a lyophilized product.

The lyophilization of the Full Emulsion according to step a6) is generally carried out on a smaller scale than the preparation of the Full Emulsion according to step a5). Typically, the lyophilization of the Full Emulsion according to step a6) is carried out on a 1-10 g scale, preferably a 2-8 g scale, more preferably a 2-6 g scale, even more preferably a 4-6 g scale, particularly preferably a 5 g scale.

Accordingly, before lyophilizing the Full Emulsion, the Full Emulsion is generally filled into suitable containers. Preferred containers are mentioned further above (under the heading "Container"). As mentioned in the preceding paragraph, the fill-weight of the Full Emulsion is typically 1-10 g, preferably 2-8 g, more preferably 2-6 g, particularly preferably 5 g.

In particularly preferred embodiments, 2-6 g (preferably 2-4 g, particularly preferably 5 g) of the Full Emulsion is filled into a container (preferably a glass container, particularly preferably a glass vial) having a volume of 8-12 mL (particularly preferably 10 mL); and is then lyophilized.

Lyophilization is a process of removal of water by sublimation. The lyophilization process consists of three steps: a freezing step, a primary drying step, and a secondary drying step.

During the freezing step, the content of the container (preferably glass vial) is frozen by lowering the temperature of the shelves in which the container (preferably glass vial) is placed.

During the primary drying step, the pressure of the chamber is lowered and the temperature of the shelves is slightly increased. The combination of lowering the chamber pressure and increasing the shelf temperature triggers the sublimation process. During the primary drying step, 80-90% of the water present in the container (preferably glass vial) is removed.

During the secondary drying step, the rest of the water is removed by further increasing the shelf temperature. At the end of the secondary drying step, the water content of the lyophilized product is preferably less than 3 wt %, more preferably less than 2 wt %, even more preferably less than 1.5 wt %, particularly preferably less than 1 wt %, based on the total weight of the lyophilized product.

According to step a7) of the method for preparing a reconstituted emulsion, water is added to the lyophilized product obtained in step a6) to obtain the reconstituted emulsion.

Particularly preferably, water for injection (WFI) is used in step a7). Alternatively, water can be added in step a7) by means of a parenteral lipid emulsion, an aqueous glucose solution, and/or an aqueous amino acid solution.

The reconstituted emulsion of the invention preferably has a pH of 6.0-9.0, more preferably 6.0-8.0, even more preferably 7.0-8.0, particularly preferably 7.0-7.5.

The reconstituted emulsion of the invention preferably has a mean volume diameter of at most 0.5 μm, more preferably at most 0.4 μm, even more preferably at most 0.3 μm, particularly preferably at most 0.2 μm. The reconstituted emulsion of the invention preferably has a mean volume diameter of 0.1-0.5 μm, more preferably 0.1-0.4 μm, even more preferably 0.15-0.30 μm, particularly preferably 0.15-0.20 μm.

Use

The lyophilized product of the invention and the reconstituted emulsion of the invention can, for example, be used as a nutritional supplement. Accordingly, in one aspect of the invention there is provided the use of a lyophilized product as defined herein as a nutritional supplement. In a further aspect of the invention there is provided the use of a reconstituted emulsion as defined herein as a nutritional supplement.

Furthermore, the lyophilized product of the invention and the reconstituted emulsion of the invention can be used as a vitamin supplement, preferably a multivitamin supplement. Accordingly, in one aspect of the invention there is provided the use of a lyophilized product as defined herein as a vitamin supplement, preferably a multivitamin supplement. In a further aspect of the invention there is provided the use of a reconstituted emulsion as defined herein as a vitamin supplement, preferably a multivitamin supplement.

The lyophilized product of the invention and the reconstituted emulsion of the invention can, for example, be used to supplement an individual with vitamins, preferably multiple vitamins. Accordingly, in one aspect of the invention there is provided the use of a lyophilized product as defined herein for supplementing an individual with vitamins, preferably multiple vitamins. In a further aspect of the invention there is provided the use of a reconstituted emulsion as defined herein for supplementing an individual with vitamins, preferably multiple vitamins. The individuals can be adults, children, or infants, preferably adults.

Furthermore, the lyophilized product of the invention and the reconstituted emulsion of the invention can be used to treat or prevent a vitamin deficiency, preferably a deficiency in multiple vitamins, in an individual. Accordingly, in one aspect of the invention there is provided the use of a lyophilized product as defined herein for treating or preventing a vitamin deficiency, preferably a deficiency in multiple vitamins, in an individual. In a further aspect of the invention there is provided a lyophilized product as defined herein for use in treating or preventing a vitamin deficiency, preferably a deficiency in multiple vitamins, in an individual. In a further aspect of the invention there is provided the use of a reconstituted emulsion as defined herein for treating or preventing a vitamin deficiency, preferably a deficiency in multiple vitamins, in an individual. In a further aspect of the invention there is provided a reconstituted emulsion as defined herein for use in treating or preventing a vitamin deficiency, preferably a deficiency in multiple vitamins, in an individual. The individuals can be adults, children, or infants, preferably adults.

Administration

The lyophilized product of the invention can be reconstituted to obtain a reconstituted emulsion, preferably a reconstituted emulsion of the invention.

The lyophilized product of the invention after reconstitution and the reconstituted emulsion of the invention are for parenteral administration, i.e. for a route of administration "other than via the gastrointestinal tract". This includes, for example, the intravenous, intra-arterial, intramuscular, intraperitoneal and subcutaneous administration. Preferably, the lyophilized product of the invention after reconstitution and the reconstituted emulsion of the invention are administered intravenously.

For example, the lyophilized product of the invention after reconstitution and the reconstituted emulsion of the invention can be added to a separate parenteral nutritional preparation and the obtained combined nutritional preparation can then be administered parenterally, preferably intravenously. Suitable parenteral nutritional preparations are known to a person skilled in the art. Such parenteral nutritional preparations may, for example, comprise fat and/or fatty acids, protein and/or amino acids, and/or carbohydrates. Examples of suitable parenteral nutritional preparations include parenteral lipid emulsions or parenteral amino acid preparations. Parenteral lipid emulsions are commercially available, for example under the trade names Intralipid, Omagaven, SMOFlipid, or Structolipid (Fresenius Kabi). Parenteral amino acid preparations are commercially available, for example under the trade names Aminoven or Aminomix (Fresenius Kabi).

Alternatively, the lyophilized product of the invention after reconstitution and the reconstituted emulsion of the invention as such can be administered parenterally, preferably intravenously. In this alternative embodiment the lyophilized product of the invention after reconstitution and the reconstituted emulsion of the invention are administered directly (i.e. without being added to a separate parenteral nutritional preparation).

Embodiments

1. Lyophilized product comprising in a single container:
   15-100 mg of an oil component; and
   the following vitamins:
   a) 2970-3630 IU vitamin A;
   b) 4.5-5.5 µg vitamin D (preferably vitamin D3);
   c) 8.2-10.0 mg vitamin E;
   d) 135-165 µg vitamin K1;
   e) 202-248 mg vitamin C;
   f) 5.4-6.6 mg vitamin B1;
   g) 3.24-3.96 mg vitamin B2;
   h) 5.4-6.6 mg vitamin B6;
   i) 4.5-5.5 µg vitamin B12;
   j) 0.54-0.66 mg vitamin B9;
   k) 13.5-16.5 mg vitamin B5;
   l) 54-66 µg vitamin B7; and
   m) 36-44 mg vitamin B3.

2. Lyophilized product according to the preceding embodiment comprising
   a) 3135-3465 IU vitamin A;
   b) 4.8-5.3 µg vitamin D (preferably vitamin D3);
   c) 8.6-9.6 mg vitamin E;
   d) 143-158 µg vitamin K1;
   e) 214-236 mg vitamin C;
   f) 5.7-6.3 mg vitamin B1;
   g) 3.4-3.8 mg vitamin B2;
   h) 5.7-6.3 mg vitamin B6;
   i) 4.8-5.3 µg vitamin B12;
   j) 0.57-0.63 mg vitamin B9;
   k) 14-16 mg vitamin B5;
   l) 57-63 µg vitamin B7; and
   m) 38-42 mg vitamin B3.

3. Lyophilized product according to any one of the preceding embodiments comprising
   a) 3300 IU vitamin A;
   b) 5.0 µg vitamin D (preferably vitamin D3);
   c) 9.1 mg vitamin E;
   d) 150 µg vitamin K1;
   e) 225 mg vitamin C;
   f) 6 mg vitamin B1;
   g) 3.6 mg vitamin B2;
   h) 6 mg vitamin B6;
   i) 5 µg vitamin B12;
   j) 0.60 mg vitamin B9;
   k) 15 mg vitamin B5;
   l) 60 µg vitamin B7; and
   m) 40 mg vitamin B3.

4. Lyophilized product according to any one of the preceding embodiments, wherein
   a) vitamin A is used in the form of retinyl palmitate;
   b) vitamin D (preferably vitamin D3) is used in the form of cholecalciferol;
   c) vitamin E is used in the form of alpha-DL-tocopherol;
   d) vitamin K1 is used in the form of phytomenadione;
   e) vitamin C is used in the form of sodium ascorbate;
   f) vitamin B1 is used in the form of thiamine hydrochloride;
   g) vitamin B2 is used in the form of riboflavin phosphate sodium salt (preferably riboflavin phosphate sodium salt dihydrate);
   h) vitamin B6 is used in the form of pyridoxine hydrochloride;
   i) vitamin B12 is used in the form of cyanocobalamine;
   j) vitamin B9 is used in the form of folic acid;
   k) vitamin B5 is used in the form of dexpanthenol;
   l) vitamin B7 is used in the form of biotin; and
   m) vitamin B3 is used in the form of niacin.

5. Lyophilized product according to any one of the preceding embodiments, wherein the oil component comprises soybean oil, olive oil, fish oil, fish oil extract, cottonseed oil, safflower oil, corn oil, sunflower oil, coconut oil, palm kernel oil, rapeseed oil, medium chain triglycerides (MCT), or mixtures thereof, preferably soybean oil.

6. Lyophilized product according to any one of the preceding embodiments comprising 30-80 mg, preferably 40-60 mg of the oil component.

7. Lyophilized product according to any one of the preceding embodiments further comprising a tonicity agent.

8. Lyophilized product according to embodiment 7, wherein the tonicity agent is selected from glycerol, propylene glycol, sorbitol, mannitol, dextrose, lactose, and sodium chloride, preferably is glycerol.

9. Lyophilized product according to embodiment 7 or 8, wherein the amount of the tonicity agent in a single container is 10-180 mg, preferably 50-150 mg, more preferably 90-130 mg.

10. Lyophilized product according to any one of the preceding embodiments further comprising an emulsifier.

11. Lyophilized product according to embodiment 10, wherein the emulsifier is egg yolk phospholipids or soybean phospholipids, preferably egg yolk phospholipids.

12. Lyophilized product according to embodiment 10 or 11, wherein the amount of the emulsifier in a single container is 10-120 mg, preferably 20-100 mg, more preferably 40-80 mg.

13. Lyophilized product according to any one of the preceding embodiments further comprising a co-emulsifier.

14. Lyophilized product according to embodiment 13, wherein the co-emulsifier is oleic acid or sodium oleate, preferably sodium oleate.

15. Lyophilized product according to embodiment 13 or 14, wherein the amount of the co-emulsifier in a single container is 0.5-4.0 mg, preferably 1.0-2.0 mg, more preferably 1.2-1.8 mg.

16. Lyophilized product according to any one of the preceding embodiments further comprising a lyoprotectant.

17. Lyophilized product according to embodiment 16, wherein the lyoprotectant is selected from trehalose, mannitol, sucrose, lactose, maltose, and glucose, preferably is trehalose.

18. Lyophilized product according to embodiment 16 or 17, wherein the amount of the lyoprotectant in a single container is 150-1000 mg, preferably 300-800 mg, more preferably 400-600 mg.

19. Lyophilized product according to any one of the preceding embodiments comprising less than 5 wt %, preferably less than 3 wt %, more preferably less than 2 wt %, even more preferably less than 1.5 wt %, particularly preferably less than 1 wt % of water, based on the total weight of the lyophilized product.

20. Lyophilized product according to any one of the preceding embodiments, wherein the container is a glass container, preferably a glass vial or a glass bottle, particularly preferably a glass vial, also particularly preferably a glass bottle.

21. Lyophilized product according to any one of the preceding embodiments, wherein the container has a volume of 5-20 mL, preferably 5-15 mL, more preferably 8-15 mL, even more preferably 8-12 mL, particularly preferably 10 mL.

22. Lyophilized product according to any one of the preceding embodiments, wherein the container is a 10 mL glass vial or a 10 mL glass bottle, preferably a 10 mL glass vial.

23. Reconstituted emulsion for parenteral application comprising in a single container:
15-100 mg of an oil component;
at least 2 ml of water; and
the following vitamins:
a) 2970-3630 IU vitamin A;
b) 4.5-5.5 µg vitamin D (preferably vitamin D3);
c) 8.2-10.0 mg vitamin E;
d) 135-165 µg vitamin K1;
e) 202-248 mg vitamin C;
f) 5.4-6.6 mg vitamin B1;
g) 3.24-3.96 mg vitamin B2;
h) 5.4-6.6 mg vitamin B6;
i) 4.5-5.5 µg vitamin B12;
j) 0.54-0.66 mg vitamin B9;
k) 13.5-16.5 mg vitamin B5;
l) 54-66 µg vitamin B7; and
m) 36-44 mg vitamin B3.

24. Reconstituted emulsion according to the preceding embodiment comprising
a) 3135-3465 IU vitamin A;
b) 4.8-5.3 µg vitamin D (preferably vitamin D3);
c) 8.6-9.6 mg vitamin E;
d) 143-158 µg vitamin K1;
e) 214-236 mg vitamin C;
f) 5.7-6.3 mg vitamin B1;
g) 3.4-3.8 mg vitamin B2;
h) 5.7-6.3 mg vitamin B6;
i) 4.8-5.3 µg vitamin B12;
j) 0.57-0.63 mg vitamin B9;
k) 14-16 mg vitamin B5;
l) 57-63 µg vitamin B7; and
m) 38-42 mg vitamin B3.

25. Reconstituted emulsion according to embodiment 23 or 24 comprising
a) 3300 IU vitamin A;
b) 5.0 µg vitamin D (preferably vitamin D3);
c) 9.1 mg vitamin E;
d) 150 µg vitamin K1;
e) 225 mg vitamin C;
f) 6 mg vitamin B1;
g) 3.6 mg vitamin B2;
h) 6 mg vitamin B6;
i) 5 µg vitamin B12;
j) 0.60 mg vitamin B9;
k) 15 mg vitamin B5;
l) 60 µg vitamin B7; and
m) 40 mg vitamin B3.

26. Reconstituted emulsion according to any one of embodiments 23 to 25, wherein
a) vitamin A is used in the form of retinyl palmitate;
b) vitamin D (preferably vitamin D3) is used in the form of cholecalciferol;
c) vitamin E is used in the form of alpha-DL-tocopherol;
d) vitamin K1 is used in the form of phytomenadione;
e) vitamin C is used in the form of sodium ascorbate;
f) vitamin B1 is used in the form of thiamine hydrochloride;
g) vitamin B2 is used in the form of riboflavin phosphate sodium salt (preferably riboflavin phosphate sodium salt dihydrate);
h) vitamin B6 is used in the form of pyridoxine hydrochloride;
i) vitamin B12 is used in the form of cyanocobalamine;
j) vitamin B9 is used in the form of folic acid;
k) vitamin B5 is used in the form of dexpanthenol;
l) vitamin B7 is used in the form of biotin; and
m) vitamin B3 is used in the form of niacin.

27. Reconstituted emulsion according to any one of embodiments 23 to 26, wherein the oil component comprises soybean oil, olive oil, fish oil, fish oil extract, cottonseed oil, safflower oil, corn oil, sunflower oil, coconut oil, palm kernel oil, rapeseed oil, medium chain triglycerides (MCT), or mixtures thereof, preferably soybean oil.

28. Reconstituted emulsion according to any one of embodiments 23 to 27 comprising 30-80 mg, preferably 40-60 mg of the oil component.

29. Reconstituted emulsion according to any one of embodiments 23 to 28 further comprising a tonicity agent.

30. Reconstituted emulsion according to embodiment 29, wherein the tonicity agent is selected from glycerol, propylene glycol, sorbitol, mannitol, dextrose, lactose, and sodium chloride, preferably is glycerol.

31. Reconstituted emulsion according to embodiment 29 or 30, wherein the amount of the tonicity agent in a single container is 10-180 mg, preferably 50-150 mg, more preferably 90-130 mg.

32. Reconstituted emulsion according to any one of embodiments 23 to 31 further comprising an emulsifier.

33. Reconstituted emulsion according to embodiment 32, wherein the emulsifier is egg yolk phospholipids or soybean phospholipids, preferably egg yolk phospholipids.

34. Reconstituted emulsion according to embodiment 32 or 33, wherein the amount of the emulsifier in a single container is 10-120 mg, preferably 20-100 mg, more preferably 40-80 mg.

35. Reconstituted emulsion according to any one of embodiments 23 to 34 further comprising a co-emulsifier.

36. Reconstituted emulsion according to embodiment 35, wherein the co-emulsifier is oleic acid or sodium oleate, preferably sodium oleate.

37. Reconstituted emulsion according to embodiment 35 or 36, wherein the amount of the co-emulsifier in a single container is 0.5-4.0 mg, preferably 1.0-2.0 mg, more preferably 1.2-1.8 mg.

38. Reconstituted emulsion according to any one of embodiments 23 to 37 further comprising a lyoprotectant.

39. Reconstituted emulsion according to embodiment 38, wherein the lyoprotectant is selected from trehalose, mannitol, sucrose, lactose, maltose, and glucose, preferably is trehalose.

40. Reconstituted emulsion according to embodiment 38 or 39, wherein the amount of the lyoprotectant in a single container is 150-1000 mg, preferably 300-800 mg, more preferably 400-600 mg.

41. Reconstituted emulsion according to any one of embodiments 23 to 40 comprising at least 3 mL, preferably at least 5 mL, more preferably at least 9 mL, even more preferably at least 10 mL of water.

42. Reconstituted emulsion according to any one of embodiments 23 to 41 comprising 2-20 ml, preferably 3-18 ml, more preferably 5-15 ml, even more preferably 8-12 ml, even more preferably 9-11 ml, particularly preferably 10 ml of water.

43. Reconstituted emulsion according to any one of embodiments 23 to 42, wherein the container is a glass container, preferably a glass vial or a glass bottle, particularly preferably a glass vial, also particularly preferably a glass bottle.

44. Reconstituted emulsion according to any one of embodiments 23 to 43, wherein the container has a volume of 5-20 mL, preferably 5-15 mL, more preferably 8-15 mL, even more preferably 8-12 mL, particularly preferably 10 mL.

45. Reconstituted emulsion according to any one of embodiments 23 to 44, wherein the container is a 10 mL glass vial or a 10 mL glass bottle, preferably a 10 mL glass vial.

46. Method for preparing a lyophilized product as defined in any one of embodiments 1 to 22, which method comprises:
    a1) preparing a water soluble vitamin solution comprising water, vitamin C, vitamin B1, vitamin B2, vitamin B6, vitamin B12, vitamin B9, vitamin B5, vitamin B7, and vitamin B3;
    a2) sterilizing the water soluble vitamin solution prepared in step a1) to obtain a sterilized water soluble vitamin solution;
    a3) preparing a Base Emulsion comprising the oil component, vitamin A, vitamin D (preferably vitamin D3), vitamin E, and vitamin K1;
    a4) sterilizing the Base Emulsion prepared in step a3) to obtain a sterilized Base Emulsion;
    a5) combining the sterilized water soluble vitamin solution obtained in step a2) and the sterilized Base Emulsion obtained in step a4) to obtain a Full Emulsion;
    a6) lyophilizing the Full Emulsion obtained in step a5) to obtain the lyophilized product.

47. Lyophilized product according to any one of embodiments 1 to 22, which is prepared by a method as defined in embodiment 46.

48. Method for preparing a reconstituted emulsion as defined in any one of embodiments 23 to 45, which method comprises adding water to a lyophilized product as defined in any one of embodiments 1 to 22.

49. Reconstituted emulsion for parenteral application obtainable by a method as defined in embodiment 48.

50. Reconstituted emulsion for parenteral application obtainable by adding water to a lyophilized product as defined in any one of embodiments 1 to 22.

51. Method for preparing a reconstituted emulsion as defined in any one of embodiments 23 to 45, which method comprises:
    a1) preparing a water soluble vitamin solution comprising water, vitamin C, vitamin B1, vitamin B2, vitamin B6, vitamin B12, vitamin B9, vitamin B5, vitamin B7, and vitamin B3;
    a2) sterilizing the water soluble vitamin solution prepared in step a1) to obtain a sterilized water soluble vitamin solution;
    a3) preparing a Base Emulsion comprising the oil component, vitamin A, vitamin D (preferably vitamin D3), vitamin E, and vitamin K1;
    a4) sterilizing the Base Emulsion prepared in step a3) to obtain a sterilized Base Emulsion;
    a5) combining the sterilized water soluble vitamin solution obtained in step a2) and the sterilized Base Emulsion obtained in step a4) to obtain a Full Emulsion;
    a6) lyophilizing the Full Emulsion obtained in step a5) to obtain a lyophilized product;
    a7) adding water to the lyophilized product obtained in step a6) to obtain the reconstituted emulsion.

52. Reconstituted emulsion according to any one of embodiments 23 to 45, which is prepared by a method as defined in embodiment 51.

53. Use of a lyophilized product as defined in any one of embodiments 1 to 22 as a nutritional supplement.

54. Use of a lyophilized product as defined in any one of embodiments 1 to 22 as a vitamin supplement, preferably a multivitamin supplement.

55. Use of a lyophilized product as defined in any one of embodiments 1 to 22 for supplementing an individual with vitamins, preferably multiple vitamins.

56. Use of a lyophilized product as defined in any one of embodiments 1 to 22 for treating or preventing a vitamin deficiency, preferably a deficiency in multiple vitamins, in an individual.

57. Lyophilized product as defined in any one of embodiments 1 to 22 for use in treating or preventing a vitamin deficiency, preferably a deficiency in multiple vitamins, in an individual.

58. Use of a reconstituted emulsion as defined in any one of embodiments 23 to 45 as a nutritional supplement.

59. Use of a reconstituted emulsion as defined in any one of embodiments 23 to 45 as a vitamin supplement, preferably a multivitamin supplement.

60. Use of a reconstituted emulsion as defined in any one of embodiments 23 to 45 for supplementing an individual with vitamins, preferably multiple vitamins.

61. Use of a reconstituted emulsion as defined in any one of embodiments 23 to 45 for treating or preventing a vitamin deficiency, preferably a deficiency in multiple vitamins, in an individual.

62. Reconstituted emulsion as defined in any one of embodiments 23 to 45 for use in treating or preventing a vitamin deficiency, preferably a deficiency in multiple vitamins, in an individual.

63. Container comprising a lyophilized product as defined in any one of embodiments 1 to 22.

64. Container according to embodiment 63, which is a glass container, preferably a glass vial or a glass bottle, particularly preferably a glass vial, also particularly preferably a glass bottle.

65. Container according to embodiment 63 or 64, which has a volume of 5-20 mL, preferably 5-15 mL, more preferably 8-15 mL, even more preferably 8-12 mL, particularly preferably 10 mL.

66. Container according to any one of embodiments 63 to 65, which is a 10 mL glass vial or a 10 mL glass bottle, preferably a 10 mL glass vial.

67. Container comprising a reconstituted emulsion as defined in any one of embodiments 23 to 45.

68. Container according to embodiment 67, which is a glass container, preferably a glass vial or a glass bottle, particularly preferably a glass vial, also particularly preferably a glass bottle.

69. Container according to embodiment 67 or 68, which has a volume of 5-20 mL, preferably 5-15 mL, more preferably 8-15 mL, even more preferably 8-12 mL, particularly preferably 10 mL.

70. Container according to any one of embodiments 67 to 69, which is a 10 mL glass vial or a 10 mL glass bottle, preferably a 10 mL glass vial.

71. Use of a lipid emulsion as a substrate for the preparation of a lyophilized product, wherein the lipid emulsion comprises 0.1-10 wt % of an oil component, based on the total weight of the lipid emulsion.

72. Use according to embodiment 71, wherein the lipid emulsion comprises 0.2-5 wt %, preferably 0.5-3 wt %, more preferably 0.5-2.5 wt % of the oil component, based on the total weight of the lipid emulsion.

73. Use according to embodiment 71 or 72, wherein the lipid emulsion comprises 0.5-1.5 wt % of the oil component, based on the total weight of the lipid emulsion.

74. Use according to embodiment 71 or 72, wherein the lipid emulsion comprises 1-2 wt % of the oil component, based on the total weight of the lipid emulsion.

75. Use according to embodiment 71 or 72, wherein the lipid emulsion comprises 2.0-2.5 wt % of the oil component, based on the total weight of the lipid emulsion.

76. Use according to any one of embodiments 71-75, wherein the oil component comprises soybean oil, olive oil, fish oil, fish oil extract, cottonseed oil, safflower oil, corn oil, sunflower oil, coconut oil, palm kernel oil, rapeseed oil, medium chain triglycerides (MCT), or mixtures thereof, preferably soybean oil.

77. Use according to any one of embodiments 71-76, wherein the lipid emulsion further comprises one or more vitamins.

78. Use according to embodiment 77, wherein the vitamins are selected from vitamin A, vitamin D (preferably vitamin D3), vitamin E, vitamin K1, vitamin C, vitamin B1, vitamin B2, vitamin B3, vitamin B5, vitamin B6, vitamin B7, vitamin B9, and vitamin B12.

79. Use according to any one of embodiments 71-76, wherein the lipid emulsion further comprises vitamin A, vitamin D (preferably vitamin D3), vitamin E, vitamin K1, vitamin C, vitamin B1, vitamin B2, vitamin B3, vitamin B5, vitamin B6, vitamin B7, vitamin B9, and vitamin B12.

80. Use according to embodiment 78 or 79, wherein vitamin A is used in the form of retinyl palmitate; vitamin D (preferably vitamin D3) is used in the form of cholecalciferol; vitamin E is used in the form of alpha-DL-tocopherol; vitamin K1 is used in the form of phytomenadione; vitamin C is used in the form of sodium ascorbate; vitamin B1 is used in the form of thiamine hydrochloride; vitamin B2 is used in the form of riboflavin phosphate sodium salt (preferably riboflavin phosphate sodium salt dihydrate); vitamin B6 is used in the form of pyridoxine hydrochloride; vitamin B12 is used in the form of cyanocobalamine; vitamin B9 is used in the form of folic acid; vitamin B5 is used in the form of dexpanthenol; vitamin B7 is used in the form of biotin; and vitamin B3 is used in the form of niacin.

81. Use according to any one of embodiment 77-80, wherein the amount of the vitamins in the lipid emulsion is 3-9 wt %, preferably 4.5-8.0 wt %, particularly preferably 5.5-7.0 wt %, based on the total weight of the lipid emulsion.

82. Use according to any one of embodiments 71-81, wherein the lipid emulsion further comprises a tonicity agent.

83. Use according to embodiment 82, wherein the tonicity agent is selected from glycerol, propylene glycol, sorbitol, mannitol, dextrose, lactose, and sodium chloride, preferably is glycerol.

84. Use according to embodiment 82 or 83, wherein the amount of the tonicity agent in the lipid emulsion is 0-5 wt %, preferably 0-3 wt %, particularly preferably 2-3 wt %, based on the total weight of the lipid emulsion.

85. Use according to any one of embodiments 71-84, wherein the lipid emulsion further comprises an emulsifier.

86. Use according to embodiment 85, wherein the emulsifier is egg yolk phospholipids or soybean phospholipids, preferably egg yolk phospholipids.

87. Use according to embodiment 85 or 86, wherein the amount of the emulsifier in the lipid emulsion is 0.5-2.5 wt %, preferably 1.0-1.5 wt %, particularly preferably 1.2 wt %, based on the total weight of the lipid emulsion.

88. Use according to any one of embodiments 71-87, wherein the lipid emulsion further comprises a co-emulsifier.

89. Use according to embodiment 88, wherein the co-emulsifier is oleic acid or sodium oleate, preferably sodium oleate.

90. Use according to embodiment 88 or 89, wherein the amount of the co-emulsifier in the lipid emulsion is 0.01-0.08 wt %, preferably 0.02-0.04 wt %, particularly preferably 0.03 wt %, based on the total weight of the lipid emulsion.

91. Use according to any one of embodiments 71-90, wherein the lipid emulsion further comprises a lyoprotectant.

92. Use according to embodiment 91, wherein the lyoprotectant is selected from trehalose, mannitol, sucrose, lactose, maltose, and glucose, preferably is trehalose.

93. Use according to embodiment 91 or 92, wherein the amount of the lyoprotectant in the lipid emulsion is 5-15 wt %, preferably 8-12 wt %, particularly preferably 10 wt %, based on the total weight of the lipid emulsion.

94. Use according to any one of embodiments 71-93, wherein the lyophilized product is a lyophilized product as defined in any one of embodiments 1-22.

The invention is further illustrated by the following examples without being limited thereby.

EXAMPLES

Example 1: Preparation of a Lyophilized Product of the Invention

The preparation of the lyophilized product of this example involves a) the preparation of a Base Emulsion, b) the preparation of a water soluble vitamin solution (WSVS), c) the preparation of a Full Emulsion, and d) the preparation of the lyophilized product.

a) Preparation of a Base Emulsion

A base emulsion having the following composition was prepared on a 2 liter scale (taking into consideration that some vitamin sources contain minor impurities, e.g. water):

1.333 wt % soybean oil
1.599 wt % purified egg yolk phospholipids (emulsifier)
0.040 wt % sodium oleate (co-emulsifier)

13.329 wt % trehalose (lyoprotectant)
0.0496 wt % vitamin A in the form of retinyl palmitate
0.00013 wt % vitamin D3 in the form of cholecalciferol
0.2503 wt % vitamin E in the form of alpha-DL-tocopherol
0.0040 wt % vitamin K1 in the form of phytomenadione
To 100 wt % water for injection The base emulsion comprises a water phase and an oil phase.

The water phase contains purified egg yolk phospholipids, sodium oleate, trehalose, and water for injection. The water phase was prepared as follows: Water for injection was heated to a temperature of 40-50° C. The rest of the raw materials were then added one-by-one to the heated water for injection, while continuously mixing. The water phase was further heated to 60-65° C. The holding time at 60-65° C. was up to 10 minutes.

The oil phase contains soybean oil, vitamin A, vitamin D3, vitamin E, and vitamin K1. The oil phase was prepared as follows: Soybean oil and all the vitamins were weighed in a beaker.

The mixture was then heated to 60-65° C., while continuously mixing. The holding time at 60-65° C. was up to 10 minutes. The weighing and heating processes of the oil phase were performed inside a dark room and while continuously flashing with inert gases, such as nitrogen or argon.

Once the water phase and oil phase were ready, a pre-emulsion was prepared by slowly adding the oil phase to the water phase at a temperature of 60-65° C. During the preparation of the pre-emulsion, a high shear mixer was used in order to finely disperse the oil phase in the continuous water phase. The pre-emulsion was mixed for 10-15 minutes.

The base emulsion was obtained by homogenizing the pre-emulsion using a high pressure homogenizer. The pre-emulsion was homogenized at 55-60° C. at a pressure of 500±5 bar in stage 1 and 50±5 bar in stage 2. A total of six homogenization cycles were used to obtain the base emulsion.

The base emulsion was sterilized using ultra high temperature (UHT) sterilization to obtain a sterile base emulsion.

b) Preparation of a Water Soluble Vitamin Solution (WSVS)

A WSVS having the following composition was prepared on a 1 liter scale (taking into consideration that some vitamin sources contain minor impurities, e.g. water):
 0.631 wt % vitamin B1 in the form of thiamine hydrochloride
 0.377 wt % vitamin B2 in the form of riboflavin phosphate sodium salt dihydrate
 3.203 wt % vitamin B3 in the form of niacin
 1.144 wt % vitamin B5 in the form of dexpanthenol
 0.585 wt % vitamin B6 in the form of pyridoxine hydrochloride
 0.00482 wt % vitamin B7 in the form of biotin
 0.052 wt % vitamin B9 in the form of folic acid
 0.00042 wt % vitamin B12 in the form of cyanocobalamine
 18.238 wt % vitamin C in the form of sodium ascorbate
 To 100 wt % water for injection The WSVS contains all the water soluble vitamins (vitamin B1, vitamin B2, vitamin B3, vitamin B5, vitamin B6, vitamin B7, vitamin B9, vitamin B12, and vitamin C) and water for injection.

The WSVS was prepared as follows: Water for injection was heated to 40-45° C. and all the vitamins were added one-by-one, except vitamin B12, while continuously mixing. Vitamin C was added after all the other vitamins were added. The WSVS, except vitamin B12, was mixed very well to assure all the vitamins were solubilized completely. Vitamin B12 was added from a previously prepared vitamin B12 stock solution. Vitamin B12 was added at a temperature of 10-15° C. at the end of the process, when the base emulsion and the WSVS were ready to be mixed. The weighing and heating processes of the WSVS were performed inside a dark room and while continuously flashing with inert gases, such as nitrogen or argon. The WSVS was sterilized using sterile filtration to obtain a sterile WSVS.

c) Preparation of a Full Emulsion

A full emulsion having the following composition was prepared on a 2 liter scale (taking into consideration that some vitamin sources contain minor impurities, e.g. water):
 1.00 wt % soybean oil
 1.20 wt % purified egg yolk phospholipids (emulsifier)
 0.03 wt % sodium oleate (co-emulsifier)
 10.00 wt % trehalose (lyoprotectant)
 0.037 wt % vitamin A in the form of retinyl palmitate
 0.0001 wt % vitamin D3 in the form of cholecalciferol
 0.188 wt % vitamin E in the form of alpha-DL-tocopherol
 0.003 wt % vitamin K1 in the form of phytomenadione
 0.158 wt % vitamin B1 in the form of thiamine hydrochloride
 0.094 wt % vitamin B2 in the form of riboflavin phosphate sodium salt dihydrate
 0.800 wt % vitamin B3 in the form of niacin
 0.286 wt % vitamin B5 in the form of dexpanthenol
 0.146 wt % vitamin B6 in the form of pyridoxine hydrochloride
 0.0012 wt % vitamin B7 in the form of biotin
 0.013 wt % vitamin B9 in the form of folic acid
 0.0001 wt % vitamin B12 in the form of cyanocobalamine
 4.555 wt % vitamin C in the form of sodium ascorbate
 To 100 wt % water for injection The full emulsion contains all the APIs and excipients. The full emulsion is the emulsion to be lyophilized.

The full emulsion was prepared as follows: The base emulsion (previously prepared as described under a)) and the WSVS (previously prepared as described under b)) were mixed at a temperature of 10-15° C. under aseptic conditions. The mixing ratio (weight ratio) of the base emulsion to the WSVS was 3.0043. The pH of the full emulsion was adjusted to 7.0-7.5 using sterile NaOH or HCl.

d) Preparation of the Lyophilized Product

A lyophilized product having the following composition (in a single container) was prepared (taking into consideration that some vitamin sources contain minor impurities, e.g. water):
 50.0 mg soybean oil
 60.0 mg purified egg yolk phospholipids (emulsifier)
 1.50 mg sodium oleate (co-emulsifier)
 500.0 mg trehalose (lyoprotectant)
 vitamin A: 1.86 mg retinyl palmitate, corresponding to 1.83 mg pure retinyl palmitate (corresponding to 3300 IU vitamin A)
 vitamin D3: 5.0 μg cholecalciferol
 vitamin E: 9.4 mg alpha-DL-tocopherol, corresponding to 9.1 mg pure alpha-DL-tocopherol
 vitamin K1: 150 μg phytomenadione
 vitamin B1: 7.9 mg thiamine hydrochloride, corresponding to 7.6 mg pure thiamine hydrochloride (corresponding to 6 mg thiamine)

vitamin B2: 4.7 mg riboflavin phosphate sodium salt dihydrate (corresponding to 3.6 mg riboflavin)
vitamin B3: 40 mg niacin
vitamin B5: 14.3 mg dexpanthenol, corresponding to 14.1 mg pure dexpanthenol (corresponding to 15 mg pantothenic acid)
vitamin B6: 7.3 mg pyridoxine hydrochloride (corresponding to 6 mg pyridoxine)
vitamin B7: 60 µg biotin
vitamin B9: 0.65 mg folic acid, corresponding to 0.60 mg pure folic acid
vitamin B12: 5 µg cyanocobalamin
vitamin C: 228 mg sodium ascorbate, corresponding to 225 mg pure sodium ascorbate The lyophilized product was prepared by lyophilizing the full emulsion (previously prepared as described under c)). The optical appearance of the lyophilized product was very good. It was obtained as a yellow homogeneous cake. The lyophilized product contained less than 3 wt % (about 2.5 wt %) of water, based on the total weight of the lyophilized product.

A lyophilizer from HOF Sonderanlagen GmbH was used, which has the following features:
Condenser capacity: 6 kg ice/24 h
Controllable shelf temperature: −45-50° C.
Minimum controllable vacuum: 0.05 mbar
Total shelf area: 0.36 m²
Number of shelves: 4
Total vial capacity (10R vials): 750

The following parameters were used to design the lyophilization process:
Glass transition temperature of the maximally freeze concentrated solute of the formulation, Tg'=−32° C.
Solid content (refers to the amount of all components, except water, in mg present in 1 mL of the full emulsion; i.e. the amount of all vitamins, the oil component, and all excipients in mg present in 1 mL of the full emulsion)=185 mg/mL
Fill-weight=5 g of the full emulsion
Container=10 mL glass vial (ISO size 10R)

The lyophilization protocol for the preparation of the lyophilized product of this example is depicted in FIG. 1. As shown in FIG. 1, the full emulsion was frozen by reducing the temperature of the shelves to −40° C. It was then held at −40° C. for some time to ensure complete solidification. In order to trigger the sublimation process, the chamber pressure was reduced to 0.1 mbar, and at the same time the shelf temperature was increased to −20° C. to compensate for the energy removed by the sublimation process. The combination of reducing the chamber pressure and increasing the shelf temperature ensures the product temperature to be below the Tg' of −32° C. and prevents the collapse of the cake. After completion of the sublimation process, the shelf temperature was increased slowly to 30° C., while keeping the chamber pressure at 0.1 mbar in order to remove the rest of the water.

The lyophilization protocol for the preparation of the lyophilized product of this example is also given in the following Table:

| Steps | Type | Heating/cooling rate [° C./min] | Shelf temperature [° C.] | Chamber pressure [mbar] | Time [min] | Group |
|---|---|---|---|---|---|---|
| 1 | Hold | ** | 10 | 1000 | 5 | Freezing |
| 2 | Ramp | 1 | 5 | 1000 | 5 | |
| 3 | Hold | ** | 5 | 1000 | 20 | |
| 4 | Ramp | 1 | −10 | 1000 | 15 | |
| 5 | Hold | ** | −10 | 1000 | 50 | |
| 6 | Ramp | 1 | −40 | 1000 | 30 | |
| 7 | Hold | ** | −40 | 1000 | 240 | |
| 8 | Ramp | 0.5 | −20 | 0.1 | 40 | Primary drying |
| 9 | Hold | ** | −20 | 0.1 | 3600 | |
| 10 | Ramp | 0.1 | −10 | 0.1 | 100 | Secondary drying |
| 11 | Hold | ** | −10 | 0.1 | 120 | |
| 12 | Ramp | 0.2 | 10 | 0.1 | 100 | |
| 13 | Hold | ** | 10 | 0.1 | 60 | |
| 14 | Ramp | 0.2 | 30 | 0.1 | 100 | |
| 15 | Hold | ** | 30 | 0.1 | 480 | |

Example 2: Preparation of a Reconstituted Emulsion of the Invention

A reconstituted emulsion was prepared by adding 10 mL of water for injection to the lyophilized product obtained in Example 1. The lyophilized product was quickly and easily rehydrated. The optical appearance of the reconstituted emulsion was very good. The reconstituted emulsion of this example has a pH of 7.0-7.5.

Example 3: Physical Stability

The physical stability of the lyophilized product and the reconstituted emulsion of the invention obtained as described in Examples 1 and 2 was investigated. The lyophilized product was stored at different temperatures (5° C., 25° C., and 40° C.) and the physical stability studies were performed at different storage times (up to 12 months). The (stored) lyophilized products were rehydrated using 10 mL water for injection to obtain the corresponding reconstituted emulsions.

Droplet size distributions and mean volume diameters of the reconstituted emulsions were determined. Droplet size distributions of the reconstituted emulsions were determined using a droplet size analysing device (Malvern Mastersizer 3000).

Figure 2:
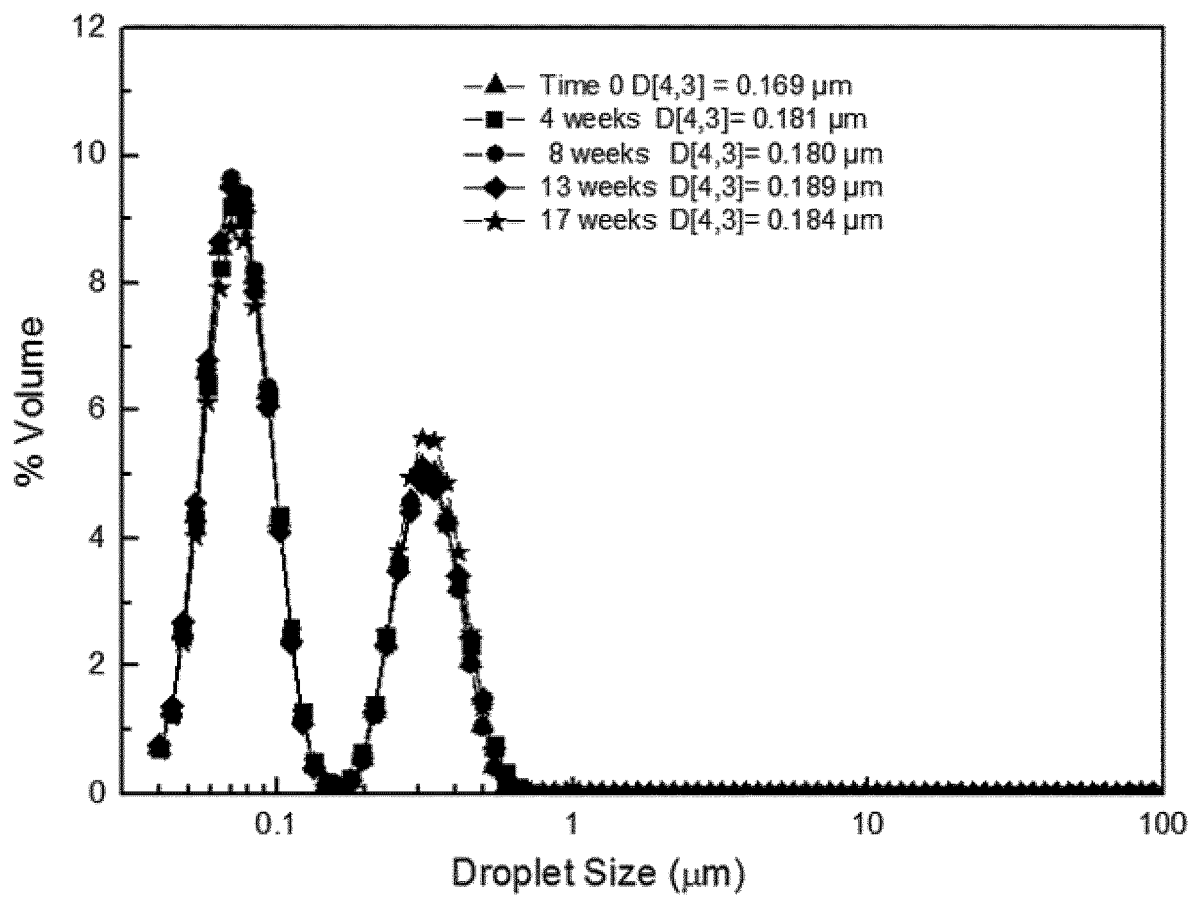
FIG. 2: Droplet size distribution of the reconstituted emulsion described in Example 2 of the present application.

Droplet size distributions of the reconstituted emulsions of this example are depicted in FIG. 2. FIG. 2 shows the droplet size distribution at selected storage times and at 25° C. storage temperature.

Volume mean droplet diameters of the reconstituted emulsions of this example at different storage times and temperatures are given in Table 3.

TABLE 3

Volume mean droplet diameters of the reconstituted emulsions of this example

| | Volume mean droplet diameter [µm] Storage temperature [° C.] | | |
|---|---|---|---|
| Storage time [weeks] | 5 | 25 | 40 |
| 0 | 0.169 | 0.169 | 0.169 |
| 4 | 0.172 | 0.181 | 0.272 |
| 8 | 0.172 | 0.180 | 0.262 |
| 13 | 0.182 | 0.189 | 0.262 |
| 17 | 0.171 | 0.184 | 0.265 |
| 34 | 0.170 | 0.187 | 0.314 |

TABLE 3-continued

Volume mean droplet diameters of the reconstituted emulsions of this example

| Storage time [weeks] | Volume mean droplet diameter [μm] Storage temperature [° C.] | | |
|---|---|---|---|
| | 5 | 25 | 40 |
| 43 | 0.185 | 0.187 | 0.265 |
| 52 | 0.179 | 0.192 | 0.353 |

In all cases the mean volume diameters were below 0.4 μm, which is below the maximum limit of mean volume diameter for parenteral lipid emulsion given by United States Pharmacopeia (USP).

Table 3 shows that prolonged storage of the lyophilized products did not adversely affect the mean volume diameters of the corresponding reconstituted emulsions. These results demonstrate that the lyophilized product of the invention and the reconstituted emulsion of the invention are physically stable. Furthermore, these results demonstrate that the lyophilized product of the invention is storage stable.

Example 4: Chemical Stability

The chemical stability of the lyophilized product and the reconstituted emulsion of the invention obtained as described in Examples 1 and 2 was investigated. The lyophilized product was stored at a temperature of 25° C. and the chemical stability studies were performed at different storage times (up to 10 months). The (stored) lyophilized products were rehydrated using 10 mL water for injection to obtain the corresponding reconstituted emulsions.

Vitamin recoveries of all 13 vitamins were determined using High Performance Liquid Chromatography (HPLC). The recovery was calculated as a relative value to the initial content of the respective vitamin in the reconstituted emulsion.

Vitamin recoveries of all 13 vitamins from the reconstituted emulsions of this example at different storage times are given in Table 4.

TABLE 4

Vitamin recoveries of all 13 vitamins from the reconstituted emulsions of this example

| Vitamin Recovery [%] | Storage time [weeks] | | | | | |
|---|---|---|---|---|---|---|
| | 0 | 4 | 8 | 13 | 34 | 43 |
| A | 100 | 107 | 109 | 108 | 100 | 101 |
| E | 100 | 100 | 100 | 99 | 101 | 102 |
| K | 100 | 100 | 100 | 98 | 98 | 99 |
| D | 100 | 104 | 105 | 105 | 93 | 104 |
| B1 | 100 | 102 | 96 | 100 | 98 | 98 |
| B2 | 100 | 103 | 100 | 102 | 99 | 99 |
| B3 | 100 | 102 | 99 | 102 | 99 | 99 |
| B5 | 100 | 102 | 99 | 101 | 99 | 98 |
| B6 | 100 | 102 | 98 | 100 | 95 | 94 |
| B7 | 100 | 104 | 101 | 99 | 103 | 99 |
| B9 | 100 | 102 | 96 | 99 | 99 | 99 |
| B12 | 100 | 99 | 100 | 99 | 98 | 99 |
| C | 100 | 108 | 105 | 107 | 97 | 99 |

Table 4 shows that all 13 vitamins were stable after prolonged storage.

These results demonstrate that the lyophilized product of the invention and the reconstituted emulsion of the invention are chemically stable. Furthermore, these results demonstrate that the lyophilized product of the invention is storage stable.

The invention claimed is:

1. A lyophilized emulsion comprising in a single container:
   15-100 mg of an oil; a phospholipid emulsifier; and the following vitamins:
   a) 2970-3630 IU vitamin A;
   b) 4.5-5.5 μg vitamin D;
   c) 8.2-10.0 mg vitamin E;
   d) 135-165 μg vitamin K1;
   e) 202-248 mg vitamin C;
   f) 5.4-6.6 mg vitamin B1;
   g) 3.24-3.96 mg vitamin B2;
   h) 5.4-6.6 mg vitamin B6;
   i) 4.5-5.5 μg vitamin B12;
   j) 0.54-0.66 mg vitamin B9;
   k) 13.5-16.5 mg vitamin B5;
   l) 54-66 μg vitamin B7; and
   m) 36-44 mg vitamin B3;
   wherein said emulsion comprises 0.1-10 wt % said oil, based on the total weight of the emulsion;
   wherein said emulsifier is present in an amount of 0.5-2.5 wt. % based on total weight of said emulsion; and
   wherein said emulsion is storage stable for 52 weeks at 25° C.

2. The lyophilized emulsion according to claim 1, wherein said product further comprises a tonicity agent.

3. The lyophilized emulsion according to claim 1, wherein said emulsifier is present in an amount of 1.0-1.5 wt. % based on total weight of said emulsion.

4. The lyophilized emulsion according to claim 1, wherein said product further comprises a co-emulsifier.

5. The lyophilized emulsion according to claim 1, wherein said product further comprises a lyoprotectant.

6. The lyophilized emulsion of claim 1, wherein:
   Vitamin A is in the form of retinyl palmitate;
   Vitamin D is present as vitamin D3;
   Vitamin E is in the form of alpha-DL-tocopherol
   Vitamin K1 is in the form of phytomenadione
   vitamin C is in the form of sodium ascorbate;
   vitamin B1 is in the form of thiamine and/or thiamine hydrochloride;
   vitamin B2 is in the form of riboflavin, riboflavin phosphates, riboflavin phosphate sodium salt, and/or riboflavin phosphate sodium salt dihydrate;
   vitamin B6 is in the form of pyridoxine and/or pyridoxine hydrochloride;
   vitamin B12 is in the form of cyanocobalamin;
   vitamin B9 is in the form of folic acid;
   vitamin B5 is in the form of pantothenic acid and/or dexpanthenol;
   vitamin B7 is in the form of biotin; and
   vitamin B3 is in the form of niacin (nicotinic acid) and/or niacinamide (nicotinamide).

7. The lyophilized emulsion according to claim 1, wherein said oil is chosen from soybean oil, olive oil, fish oil, fish oil extract, cottonseed oil, safflower oil, corn oil, sunflower oil, coconut oil, palm kernel oil, rapeseed oil, medium chain triglycerides (MCT), and mixtures thereof.

8. The lyophilized emulsion according to claim 1, wherein said emulsion comprises 0.2-5 wt % said oil, based on the total weight of the emulsion.

9. A reconstituted emulsion for parenteral application comprising in a single container:
15 to 100 mg of an oil; a phospholipid emulsifier;
at least 2 ml of water; and
the following vitamins:
a) 2970-3630 IU vitamin A;
b) 4.5-5.5 g vitamin D;
c) 8.2-10.0 mg vitamin E;
d) 135-165 mg vitamin K1;
e) 202-248 mg vitamin C;
f) 5.4-6.6 mg vitamin B1;
g) 3.24-3.96 mg vitamin B2;
h) 5.4-6.6 mg vitamin B6;
i) 4.5-5.5 µg vitamin B12;
j) 0.54-0.66 mg vitamin B9;
k) 13.5-16.5 mg vitamin B5;
l) 54-66 µg vitamin B7; and
m) 36-44 mg vitamin B3 wherein said emulsion comprises 0.1-10 wt % said oil, based on the total weight of the emulsion; and wherein said emulsifier is present in an amount of 0.5-2.5 wt. % based on total weight of said emulsion.

10. The emulsion of claim 9, wherein:
Vitamin A is in the form of retinyl palmitate;
Vitamin D is present as vitamin D3;
Vitamin E is in the form of alpha-DL-tocopherol
Vitamin K1 is in the form of phytomenadione
vitamin C is in the form of sodium ascorbate;
vitamin B1 is in the form of thiamine and/or thiamine hydrochloride;
vitamin B2 is in the form of riboflavin, riboflavin phosphates, riboflavin phosphate sodium salt, and/or riboflavin phosphate sodium salt dihydrate;
vitamin B6 is in the form of pyridoxine and/or pyridoxine hydrochloride;
vitamin B12 is in the form of cyanocobalamin;
vitamin B9 is in the form of folic acid;
vitamin B5 is in the form of pantothenic acid and/or dexpanthenol;
vitamin B7 is in the form of biotin; and
vitamin B3 is in the form of niacin (nicotinic acid) and/or niacinamide (nicotinamide).

11. A method for preparing a lyophilized emulsion, said method comprises:
a1) preparing a water soluble vitamin solution comprising water, vitamin C, vitamin B1, vitamin B2, vitamin B6, vitamin B12, vitamin B9, vitamin B5, vitamin B7, and vitamin B3;
a2) sterilizing the water soluble vitamin solution prepared in step a1) to obtain a sterilized water soluble vitamin solution;
a3) preparing a Base Emulsion comprising the oil component, vitamin A, vitamin D, vitamin E, and vitamin K1;
a4) sterilizing the Base Emulsion prepared in step a3) to obtain a sterilized Base Emulsion;
a5) combining the sterilized water soluble vitamin solution obtained in step a2) and the sterilized Base Emulsion obtained in step a4) to obtain a Full Emulsion;
a6) lyophilizing the Full Emulsion obtained in step a5) to obtain the lyophilized product;
wherein said lyophilized product comprises in a single container:
0.15 to 100 mg of an oil; a phospholipid emulsifier; and the following vitamins:
a) 2970-3630 IU vitamin A;
b) 4.5-5.5 µg vitamin D (preferably vitamin D3);
c) 8.2-10.0 mg vitamin E;
d) 135-165 µg vitamin K1;
e) 202-248 mg vitamin C;
f) 5.4-6.6 mg vitamin B1;
g) 3.24-3.96 mg vitamin B2;
h) 5.4-6.6 mg vitamin B6;
i) 4.5-5.5 µg vitamin B12;
j) 0.54-0.66 mg vitamin B9;
k) 13.5-16.5 mg vitamin B5;
l) 54-66 µg vitamin B7; and
m) 36-44 mg vitamin B3 wherein said emulsion comprises 0.1-10 wt % said oil, based on the total weight of the emulsion; wherein said emulsifier is present in an amount of 0.5-2.5 wt. % based on total weight of said emulsion; and wherein said emulsion is storage stable for 52 weeks at 25° C.

12. The method according to claim 11, said method further comprising adding water to said lyophilized product.

13. A method of providing a vitamin supplement to an individual, said method comprising administering to said individual a reconstituted emulsion according to claim 6.

14. The method of claim 13, wherein said reconstituted emulsion is administered to treat a vitamin deficiency in said individual.

* * * * *